United States Patent [19]
Robison et al.

[11] Patent Number: 6,146,876
[45] Date of Patent: Nov. 14, 2000

[54] 22025, A NOVEL HUMAN CYCLIC NUCLEOTIDE PHOSPHODIESTERASE

[75] Inventors: Keith E. Robison, Wilmington; Rosana Kapeller-Libermann, Chestnut Hill; David White, Holbrook, all of Mass.

[73] Assignee: Millennium Pharmaceuticals, Inc., Cambridge, Mass.

[21] Appl. No.: 09/330,970

[22] Filed: Jun. 11, 1999

Related U.S. Application Data

[63] Continuation-in-part of application No. 09/277,423, Mar. 26, 1999.

[51] Int. Cl.$^7$ .............................. C12N 1/20; C12N 15/00; C07H 21/04
[52] U.S. Cl. .................. 435/243; 435/252.3; 435/320.1; 536/23.2; 536/23.5; 536/24.31
[58] Field of Search ................... 536/23.2, 23.5, 536/24.31; 435/183, 243, 252.3, 320.1

[56] References Cited

U.S. PATENT DOCUMENTS

| | | | |
|---|---|---|---|
| 5,527,896 | 6/1996 | Wigler et al. | 536/23.5 |
| 5,702,936 | 12/1997 | Beavo et al. | |
| 5,798,246 | 8/1998 | Au-Young et al. | |
| 5,851,784 | 12/1998 | Owens et al. | |

OTHER PUBLICATIONS

Michaeli, Tamar, et al., "Isolation and Characterization of a Previously Undetected Human cAMP Phosphodiesterase by Complementation of cAMP Phosphodiesterase–deficient *Saccharomyces cervisiae*," The Journal Of Biological Chemistry, vol. 268, No. 17, pp. 12, Jun. 1993.

Bloom, T., et al., "Identification and tissue–specific expression of PDE7 phosphodiesterase splice variants," Proceedings of the National Academy of Sciences, USA, vol. 93, pp. 14188–14192, Nov. 1996.

ID CN7A_HUMAN, Jun. 1993.

ID CN7A_MOUSE, Nov. 1996.

Houslay et al. (1997), "Tailoring cAMP–Signalling Responses Through Isoform Multiplicity", *TiBS* 22:217:224.

Bloom et al. (1996), "Identification and Tissue–Specific Expression of PDE7 Phosphodiesterase Splice Variants", *Proc. Natl. Acad. Sci. USA* 93:14188–14192.

Han et al. (1997), "Alternative Splicing of the High Affinity cAMP–Specific Phosphodiesterase (PDE7A) mRNA in Human Skeletal Muscle and Heart", *The Journal of Biological Chemistry* 272 (26):16152–16157.

Beavo (1995), "Cyclic Nucleotide Phosphodiesterases: Functional Implications of Multiple Isoforms", *Physiological Reviews* 75(4):725–748.

DNA Blast Analysis Against NUC, PrevPatent Databases.

Protein Blast Analysis Against PNU, Patent Databases.

*Primary Examiner*—Bradley L. Sisson
*Attorney, Agent, or Firm*—Alston & Bird LLP

[57] ABSTRACT

The present invention relates to a newly identified human cyclic nucleotide phosphodiesterase belonging to the superfamily of mammalian phosphodiesterases. The invention also relates to polynucleotides encoding the phosphodiesterase. The invention further relates to methods using the phosphodiesterase polypeptides and polynucleotides as a target for diagnosis and treatment in phosphodiesterase-mediated or -related disorders. The invention further relates to drug-screening methods using the phosphodiesterase polypeptides and polynucleotides to identify agonists and antagonists for diagnosis and treatment. The invention further encompasses agonists and antagonists based on the phosphodiesterase polypeptides and polynucleotides. The invention further relates to procedures for producing the phosphodiesterase polypeptides and polynucleotides.

8 Claims, 16 Drawing Sheets

```
Sequence length 2202
          10        20        30        40        50        60        70
GGAGGGCCTGAAGAGACAGGGAGGTTGTGCCAGGCTGGAGGAGGCTTGTCTTTCCGAAGCTGGAGAGGATCTTACGGGG
     80        90       100       110       120       130       140       150
GTTCGCTTTTCCCTGCCTGGGAAGAATTTCCCCTGTGGTAGCAGCAGCAGCAGCAGCAGAAGCAGAAACAGCAGCAGCA
    160       170       180       190       200       210       220   M   P   V
GCAACAGCAGCAGCAGCAGCAGCACCACCACCACCACTACCTCCTCTTCTGGGGCACAAGACAGA ATG CCT GTG    232
 L   E   R   Y   F   H   P   A   E   L   G   R   R   W   T   G   P   E   G   V
CTA GAG CGA TAT TTC CAC CCA GCA GAG CTA GGC AGG AGG TGG ACA GGC CCA GAA GGT GTG   292
 L   P   S   S   P   G   S   R   P   G   C   Q   Q   G   P   L   P   W   D   L
CTG CCC TCC TCC CCG GGA AGC CGG CCG GGG TGC CAG CAG GGG CCG CTG CCC TGG GAC TTG   352
 P   E   M   I   R   M   V   K   L   V   W   K   S   K   S   E   L   Q   A   T
CCA GAG ATG ATC AGG ATG GTA AAG CTG GTT TGG AAA TCC AAA AGT GAG CTG CAG GCG ACC   412
 K   Q   R   G   I   L   D   N   E   D   A   L   R   S   F   P   G   D   I   R
AAA CAG AGA GGC ATT CTG GAC AAT GAA GAT GCT CTC CGC AGC TTT CCA GGA GAT ATA CGA   472
 L   R   G   Q   T   G   V   R   A   E   R   R   G   S   Y   P   F   I   D   F
CTA AGG GGT CAG ACG GGG GTT CGT GCT GAA CGC CGT GGC TCC TAC CCA TTC ATT GAC TTC   532
 R   L   L   N   S   T   T   Y   S   G   E   I   G   T   K   K   K   V   K   R
CGC CTA CTT AAC AGT ACA ACA TAC TCA GGG GAG ATT GGC ACC AAG AAA AAG GTG AAA AGA   592
 L   L   S   F   Q   R   Y   F   H   A   S   R   L   L   R   G   I   I   P   Q
CTA TTA AGC TTT CAA AGA TAC TTC CAT GCA TCA AGG CTG CTT CGT GGA ATT ATA CCA CAA   652
 A   P   L   H   L   L   D   E   D   Y   L   G   Q   A   R   H   M   L   S   K
GCC CCT CTG CAC CTG CTG GAT GAA GAC TAC CTT GGA CAA GCA AGG CAT ATG CTC TCC AAA   712
 V   G   M   W   D   F   D   I   F   L   F   D   R   L   T   N   G   N   S   L
GTG GGA ATG TGG GAT TTT GAC ATT TTC TTG TTT GAT CGC TTG ACA AAT GGA AAC AGC CTG   772
 V   T   L   L   C   H   L   F   N   T   H   G   L   I   H   H   F   K   L   D
GTA ACA CTG TTG TGC CAC CTC TTC AAT ACC CAT GGA CTC ATT CAC CAT TTC AAG TTA GAT   832
 M   V   T   L   H   R   F   L   V   M   V   Q   E   D   Y   H   S   Q   N   P
ATG GTG ACC TTA CAC CGA TTT TTA GTC ATG GTT CAA GAA GAT TAC CAC AGC CAA AAC CCG   892
 Y   H   N   A   V   H   A   A   D   V   T   Q   A   M   H   C   Y   L   K   E
TAT CAC AAT GCT GTT CAC GCA GCC GAC GTC ACC CAG GCC ATG CAC TGC TAC CTG AAA GAG   952
 P   K   L   A   S   F   L   T   P   L   D   I   M   L   G   L   L   A   A   A
CCA AAG CTT GCC AGC TTC CTC ACG CCT CTG GAC ATC ATG CTT GGA CTG CTG GCT GCA GCA   1012
 A   H   D   V   D   H   P   G   V   N   Q   P   F   L   I   K   T   N   H   H
GCA CAC GAT GTG GAC CAC CCA GGG GTG AAC CAG CCA TTT TTG ATA AAA ACT AAC CAC CAT   1072
 L   G   A   L   Y   Q   N   M   S   V   L   E   N   H   H   W   R   S   T   I
CTT GCA AAC CTA TAT CAG AAT ATG TCT GTG CTG GAG AAT CAT CAC TGG CGA TCT ACA ATT   1132
 G   M   L   R   E   S   R   L   L   A   H   L   P   K   E   M   T   Q   D   I
GGC ATG CTT CGA GAA TCA AGG CTT CTT GCT CAT TTG CCA AAG GAA ATG ACA CAG GAT ATT   1192
 E   Q   Q   L   G   S   L   I   L   A   T   D   I   N   R   Q   N   E   F   L
GAA CAG CAG CTG GGC TCC TTG ATC TTG GCA ACA GAC ATC AAC AGG CAG AAT GAA TTT TTG   1252
```

FIG. 1A.

```
 T   R   L   K   A   H   L   H   N   K   D   L   R   L   E   D   A   Q   D   R
ACC AGA TTG AAA GCT CAC CTC CAC AAT AAA GAC TTA AGA CTG GAG GAT GCA CAG GAC AGG  1312
 H   F   M   L   Q   I   A   W   K   C   A   D   I   C   N   P   C   R   I   W
CAC TTT ATG CTT CAG ATC GCT TGG AAG TGT GCT GAC ATT TGC AAT CCT TGT AGA ATC TGG  1372
 E   M   S   K   Q   W   S   E   R   V   C   E   E   F   Y   R   Q   G   E   L
GAG ATG AGC AAG CAG TGG AGT GAA AGG GTC TGT GAA GAA TTC TAC AGG CAA GGT GAA CTT  1432
 E   Q   K   F   E   L   E   I   S   P   L   C   N   Q   Q   K   D   S   I   P
GAA CAG AAA TTT GAA CTG GAA ATC AGT CCT CTT TGT AAT CAA CAG AAA GAT TCC ATC CCT  1492
 S   I   Q   I   G   F   M   S   Y   I   V   E   P   L   F   R   E   W   A   H
AGT ATA CAA ATT GGT TTC ATG AGC TAC ATC GTG GAG CCG CTC TTC CGG GAA TGG GCC CAT  1552
 F   T   G   N   S   T   L   S   E   N   M   L   G   H   L   A   H   N   K   A
TTC ACG GGT AAC AGC ACC CTG TCG GAG AAC ATG CTG GGC CAC CTC GCA CAC AAC AAG GCC  1612
 Q   W   K   S   L   L   P   R   Q   H   R   S   R   G   S   S   G   S   G   P
CAG TGG AAG AGC CTG TTG CCC AGG CAG CAC AGA AGC AGG GGC AGC AGT GGC AGC GGG CCT  1672
 D   H   D   H   A   G   Q   G   T   E   S   E   E   Q   E   G   D   S   P   *
GAC CAC GAC CAC GCA GGC CAA GGG ACT GAG AGC GAG GAG CAG GAA GGC GAC AGC CCC TAG  1732
GGGCCGGCCCAACTTAGACGCGGCTCTCCTCCGGCAGGGCCCCCAGAGGGCAGAAGCAGCGTGGAGGGGCCCTCACGCA

GCAGCCCAGCCACTTTCTGAGTGTTGTCCTGGGGCTCTTTGGAACGCCATCTTCCTCCCACTTACCTGCCTCCCCTCCT

TTTCGCAAATGTACAGAAGCCATTTGTCACCTCAGCATTCGCTGCCGAAATGAGCAACTCCATTCAGTAAGCTGGGAGC

TGATCCCACGGGCAGGCTCTCCCTGCTCCAGGAGAAGACTAGGAGGAAGAATGAGGTGCTCCTGCCGTGTCCGCCTTGT

TCCGGGTCGCACTGGAACAGGCAGCAATTCCTAAGTCCGGAGCGTTTGAGCGTTTGCTATCTGACTGCTGATCTGCGTG

ACAGAAACACCAGCATATTTGCAACGCCAAGGATATTGGTCTTAAAGTGCAAGAACACAAATGAGAGTGTGAAGA
```

FIG. 1B.

```
PDEase    PF00233  3'5'-cyclic nucleotide phosphodieste   211.4   3.3e-73   1
Parsed for domains:
Model      Domain  seq-f seq-t   hmm-f hmm-t    score    E-value
PDEase     1/1     224   462 ..    1    279  []  211.4   3.3e-73
Alignments of top-scoring domains:
PDEase: domain 1 of 1, from 224 to 462:  scor 211.4, E = 3.3e-73
                    *->YHNwiHAfdVtQtthlLlltlaleryLtdlEvLalvfAAaiHDvDHr
                       YHN  HA+dVtQ++h+ l+ ++l  Lt+l + + + AAa HDvDH+
    sequence27  224  YHNAVHAADVTQAMHCYLKEPKLASFLTPLDIMLGLLAAAAHDVDHP 270

GTnNsFqinsLqkSeLAILYndegSVLEnHHlaqafkLLqdEecnIfqNL
                    G+n  F+i++ +  LA LY +  SVLEnHH  +++ +L+  e  + +L
    sequence27  271 GVNQPFLIKT--NHHLANLYQNM-SVLENHHWRSTIGMLR--ESRLLAHL 315 skkdfrtlrdlvieaILAATDmslHlqklkdlktmveqkkvyetgvEWtqY
                    +k   +++         ILATD+     l++lk  +  k           +
    sequence27  316 PKEMTQDIEQQLGSLILATDINRQNEFFLTRLKAHLHNK----------DL 355 lldnythkilllsllmtAADLSnpTKpwslskRwAelimeEFFeQGDlEr
                    l + +++    l+   ++AD+ np  +w+ sk+w e++  eEF++QG lE
    sequence27  356 RLEDAQDRHFMLQIAWKCADICNPCRIWEMSKQWSERVCEEFYRQGELEQ 405 elGldrpspmcDRtsAayvpksQvgFidfIvePvfkllLadvvekGRttse
                    l  +sp+c  + +++p  Q+gF+ +IveP+f  ++a ++
    sequence27  406 KFELE-ISPLCNQQK-DSIPSIQEGFMSYIVEPLFREWAHFTGN------ 447 aiDanhLCWvaLDeevRnddiaplldriednR<-*
                        +   +l +++ n+
    sequence27  448 -----------------STLSENMLGHLAHNK
```

FIG. 2.

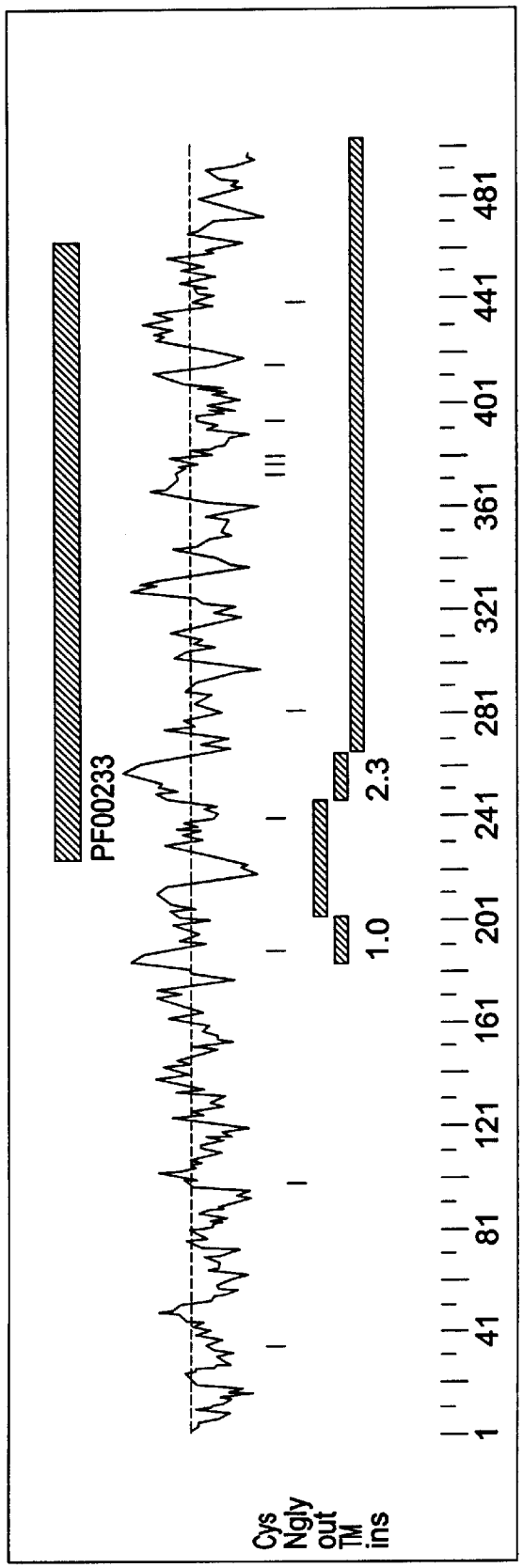

FIG. 4.

```
>sequence2741
MPVLERYFHPAELGRRWTGPEGVLPSSPGSRPGCQQGPLPWDLPEMIRMVKLVWKSKSEL
QATKQRGILDNEDALRSFPGDIRLRGQTGVRAERRGSYPFIDFRLLNSTTYSGEIGTKKK
VKRLLSFQRYFHASRLLRGIIPQAPLHLLDEDYLGQARHMLSKVGMWDFDIFLFDRLTNG
NSLVTLLCHLFNTHGLIHHFKLDMVTLHRFLVMVQEDYHSQNPYHNAVHAADVTQAMHCY
LKEPKLASFLTPLDIMLGLLAAAHDVDHPGVNQPFLIKTNHHLANLYQNMSVLENHHWR
STIGMLRESRLLAHLPKEMTQDIEQQLGSLILATDINRQNEFLTRLKAHLHHKDLRLEDA
QDRHFMLQIAWKCADICNPCRIWEMSKQWSERVCEEFYRQGELEQKFELEISPLCNQQKD
SIPSIQIGFMSYIVEPLFREWAHFTGNSTLSENMLGHLAHNKAQWKSLLPRQHRSRGSSG
SGPDHDHAGQGTESEEQEGDSP
```

Transmembrane Segments Predicted by MEMSAT

| Start | End | Orient | Score |
|---|---|---|---|
| 183 | 200 | ins-->out | 1.0 |
| 246 | 264 | out-->ins | 2.3 |

>sequence2741
MPVLERYFHPAELGRRWTGPEGVLPSSPGSRPGCQQGPLPWDLPEMIRMVKLVWKSKSEL
QATKQRGILDNEDALRSFPGDIRLRGQTGVRAERRGSYPFIDFRLLNSTTYSGEIGTKKK
VKRLLSFQRYFHASRLLRGIIPQAPLHLLDEDYLGQARHMLSKVGMWDFDIFLFDRLTNG
NSLVTLLCHLFNTHGLIHHFKLDMVTLHRFLVMVQEDYHSQNPYHNAVHAADVTQAMHCY
LKEPKLASFLTPLDIMGLLAAAAHDVDHPGVNQPFLIKTNHHLANLYQNMSVLENHHWR
STIGMLRESRLLAHLPKEMTQDIEQQLGSLILATDINRQNEFLTRLKAHHLHNKDLRLEDA
QDRHFMLQIAWKCADICNPCRIWEMSKQWSERVCEEFYRQGELEQKFELEISPLCNQQKD
SIPSIQIGFMSYIVEPLFREWAHFTGNSTLSENMLGHLAHNKAQWKSLLPRQHRSRGSSG
SGPDHDHAGQGTESEEQEGDSP Prosite Pattern Matches for sequence2741

>PS00001/PDOC00001/ASB_GLYCOSYLATION N-glycosylation site.

Query: 107    NSTT    110

Query: 290    NMSV    293

Query: 447    NSTL    450

FIG. 5A.

>PS00002/PDOC00002/GLYCOSAMINOGLYCAN Glycosaminoglycan attachment site.
    RU    Additional rules:
    RU    There must be at least two acidic amino acids (Glu or Asp) from -2 to
    RU    -4 relative to the serine.

Query: 479    SGSG    482

>PS00004/PDOC00004/CAMP_PHOSPHO_SITE cAMP- and cGMP-dependent protein kinase phosphorylation site.

Query: 15    SGSG    18
Query: 94    RRGS    97

>PS00005/PDOC00005/PKC_PHOSPHO_SITE Protein kinase C phosphorylation site.

Query: 117    TKK    119
Query: 390    SER    392

>PS00006/PDOC00006/CK2_PHOSPHO_SITE Casein kinase II phosphorylation site.

Query: 18    TGPE    21
Query: 56    SKSE    59
Query: 251    TPLD    254
Query: 292    SVLE    295
Query: 449    TLSE    452
Query: 481    SGPD    484
Query: 492    TESE    495

>PS00007/PDOC00007/TYR_PHOSPHO_SITE Tyrosine kinase phosphorylation site.

Query: 392    RVCEEFY   398

>PS00008/PDOC00008/MYRISTYL N-myristoylation site.

Query: 22    GVLPSS    27
Query: 29    GSRPGC    34
Query: 67    GILDNE    72
Query: 258    GLLAAA    263
Query: 477    GSSGSG    482

>PS00009/PDOC00009/AMIDATION Amidation site.

Query: 13    LGRR    16

FIG. 5B.

22025c12, 3336 bases, 672 check
[Strand]

```
  1   GAGGGCCTGA AGACACAGGG AGGTTGTGCC AGGCTGGAGG

41   AGGCTTGTCT TTCCGAAGCT GGAGAGGATC TTACGGGGGT

81   TCGCTTTTCC CTGCCTGGGA AGAATTTCCC CTGTGGTAGC

121   AGCAGCAGCA GCAGCAGAAG CAGAAACAGC AGCAGCAGCA

161   ACAGCAGCAG CAGCAGCAGC ACCACCACCA CCACTACCTC

201   CTCTTCTGGG GCACAAGACA GAATGCCTGT GCTAGAGCGC
                                     METProVal LeuGluArg
241   TATTTCCACC CAGCAGAGCT AGGCAGGAGG TGGACAGGCC
      ThyPheHisPro AlaGluLeu GlyArgArg TryThrGlyP
281   CAGAAGGTGT GCTGCCCTCC TCCCCGGGAA GCCGGCCGGG
      roGluGlyVal LeuProSer SerProGlySer ArgProGl
321   GTGCCAGCAG GGGCCGCTGC CCTGGGACTT GCCAGAGATG
      yCysGlnGln GlyProLeuPro TrpAspLeu ProGluMET
361   ATCAGGATGG TAAAGCTGGT TTGGAAATCC AAAAGTGAGC
      IleArgMETVal LysLeuVal TrpLysSer LysSerGluL
401   TGCAGGCGAC CAAACAGAGA GGCATTCTGG ACAATGAAGA
      euGlnAlaThr LysGlnArg GlyIleLeuAsp AsnGluAs
441   TGCTCTCCGC AGCTTTCCAG GAGATATACG ACTAAGGGGT
      pAlaLeuArg SerPheProGly AspIleArg LeuArgGly
481   CAGACGGGGG TTCGTGCTGA ACGCCGTGGC TCCTACCCAT
      GlnThrGlyVal ArgAlaGlu ArgArgGly SerTyrProP
521   TCATTGACTT CCGCCTACTT AACAGTACAA CATACTCAGG
      heIleAspPhe ArgLeuLeu AsnSerThrThr TyrSerGl
561   GGAGATTGGC ACCAAGAAAA AGGTGAAAAG ACTATTAAGC
      yGluIleGly ThrLysLysLys ValLysArg LeuLeuSer
```

FIG. 6A.

22025c12, 3336 bases, 672 check
[Strand]

```
 601   TTTCAAAGAT ACTTCCATGC ATCAAGGCTG CTTCGTGGAA
       PheGlnArgTyr PheHisAla SerArgLeu LeuArgGlyI
 641   TTATACCACA AGCCCCTCTG CACCTGCTGG ATGAAGACTA
       leIleProGln AlaProLeu HisLeuLeuAsp GluAspTy
 681   CCTTGGACAA GCAAGGCATA TGCTCTCCAA AGTGGGAATG
       rLeuGlyGln AlaArgHisMET LeuSerLys ValGlyMET
 721   TGGGATTTTG ACATTTTCTT GTTTGATCGC TTGACAAATG
       TrpAspPheAsp IlePheLeu PheAspArg LeuThrAsnG
 761   GAAACAGCCT GGTAACACTG TTGTGCCACC TCTTCAATAC
       lyAsnSerLeu ValThrLeu LeuCysHisLeu PheAsnTh
 801   CCATGGACTC ATTCACCATT TCAAGTTAGA TATGGTGACC
       rHisGlyLeu IleHisHisPhe LysLeuAsp METValThr
 841   TTACACCGAT TTTAGTCAT GGTTCAAGAA GATTACCACA
       LeuHisArgPhe LeuValMET ValGlnGlu AspTyrHisS
 881   GCCAAAACCC GTATCACAAT GCTGTTCACG CAGCCGACGT
       erGlnAsnPro TyrHisAsn AlaValHisAla AlaAspVa
 921   CACCCAGGCC ATGCACTGCT ACCTGAAAGA GCCAAAGCTT
       lThrGlnAla METHisCysTyr LeuLysGlu ProLysLeu
 961   GCCAGCTTCC TCACGCCTCT GGACATCATG CTTGGACTGC
       AlaSerPheLeu ThrProLeu AspIleMET LeuGlyLeuL
1001   TGGCTGCAGC AGCACACGAT GTGGACCACC CAGGGGTGAA
       euAlaAlaAla AlaHisAsp ValAspHisPro GlyValAs
1041   CCAGCCATTT TTGATAAAAA CTAACCACCA TCTTGCAAAC
       nGlnProPhe LeuIleLysThr AsnHisHis LeuAlaAsn
1081   CTATATCAGA ATATGTCTGT GCTGGAGAAT CATCACTGGC
       LeuTyrGlnAsn METSerVal LeuGluAsn HisHisTrpA
1121   GATCTACAAT TGGCATGCTT CGAGAATCAA GGCTTCTTGC
       rgSerThrIle GlyMETLeu ArgGluSerArg LeuLeuAl
1161   TCATTTGCCA AAGGAAATGA CGTAAGTGCT GCCGAGATGA
       aHisLeuPro LysGluMETThr STP
```

FIG. 6B.

22025c12, 3336 bases, 672 check
[Strand]

```
1201   AACATACTGA TGTGCATGCA GTAAAGATAA GCCACTTTCT

1241   CTAGGGCAGG CTTGGGACCT TTTGCGTGAA TGGCAGAGAG

1281   CCCCCCGCT GTACTTCCTG CCTGCACTGA GCTGTCTATC

1321   AGAGGAGATT TGGTGTCAGT TACAGCAACC CAGAAACCAA

1361   AATCTCTCTG TGTGCTTTGA AAGGGCCTTG CAGAGTCAAT

1401   GACCTACAGT CAGGAAAAGG GATAATAAAC AGCTCTCAGT

1441   TTTCACACGC TTCAGTATCA GTGCTCGACT TTGCCAAATT

1481   CCCGACCTTT AGTTTAGCAA AATTGTCCTT CCATGTAGCT

1521   CCAAATAGTA AATATTTATC AAGAAGGAAC CCAGGCATTC

1561   TAAAGCTAGA GTTCAAAAAA GTATATTTTG TAATTGCTAG

1601   TCTCAGCAAA AATAGAAGTC AGAAATTCTT TTCTAAAATG

1641   TCTTTTGCTA AGTAATTGAA ATGGCCCTAG CATTTTTTC

1681   ACCAATTAAT TTACCTTACG TCTCTTGCAC TTTAAACAGA

1721   AGGGGAGACA CTCATTTTCT GGTTCACTAT TTGATAGCCA

1761   TGGTATGTAG GCTGAGTCCC ACTAAATCTG AGGCCATTGT
```

FIG. 6C.

22025c12, 3336 bases, 672 check
[Strand]

1801 TTCATTTTCC TGGTGGCCCC AAGTTAGCTG CTAATACTGT

1841 CTTCCAAGGC CACCATTAAT TCTGATCTGT TTAATGAACA

1881 CGTGCAGAAC CCAAGAAACC TAGGTGAAAA GAGTACATAG

1921 ATTGCTGTAC CCTTCTTCAA GACAAGCACA TAACTTGAGG

1961 TCAAGGACCA AGTGCTGTCT CCCAACTGAA CAAGCAGTAT

2001 ACTCTGGGTT GTGGATTGAT TCCTGGCCCT CTGATTTGAT

2041 CTCATGCTGT TTCCTAGCAC CCAGAGGAAT GTGAAATTTG

2081 CAGGAGGAAT TTCAGTTCTG ATAAATTTTT ACTCCCTGGA

2121 ACTAAATAAA ACCAGTTCTC GTGCATGGAA TAAAAACTTA

2161 TGCCTCTTAC TAGAATAATA AATTGCAAAG ATTGAAAGAA

2201 TTAAATGCAA AAAGAACTAA AAACTAGAGC AAAAGATCAA

2241 GTGAGAAGAA GAAAAGAGGA GGTAAGGAGA GAGACAAGGA

2281 AGAAAGAAGG AGAAGGAAAG GAAGAATAGT GAGGACAGGA

2321 AAGAAGAAAA TGCAAGGGAA ATGGGAAAGG ACTCTGGGGT

2361 GACCAGACTT CTCCTGGTCA GTACCTGCAT TCATCCTGTT

FIG. 6D.

22025c12, 3336 bases, 672 check
[Strand]

2401 TGTTACTCAA TATTTCTTTC CTAAAATATT CATTTCACAT

2441 CTATGGATTC CAATGAAAAA TATATTTTTA TGTGTCTTTG

2481 TGGAACACAG TGTTATAAAT TGTTTTTGCC AGAAGAATAA

2521 TTGTTATACA ATAATATATG TGAAAACTTT ATTACAAAAG

2561 CCATTATCAT AATCATTATT ATTCCTTCTA TCACAGGTAA

2601 ATGCTTTAAT GTCATTTTTC TGATTTTAAA AGTAGGGCAG

2641 GTTAATTGTA GAAAGTAAGG AAAATTCAGG AAAGTGTTAG

2681 TTTGAACTAT GTGAAGTTGC TCTTTTTAAG GGCCAAAAAC

2721 AGGAGACTTT TAGCACTTTC ATATGTTTCA GCTTGATATG

2761 AAAGAGAAAA CTGAAACTGC TAGTAATCCT GCCATCCAGG

2801 TATAGTTCAT GTTAACCTGG CTAGTTTATT TTCTTTTAGT

2841 CTTTTTTCAA TACAAACTTA TTTTAACAAA ATATGATTAN

2881 ATTTGGGGAA CTTATTTTAC AGTTTACGTC CTGAAATTTT

2921 TTATTTACAA TAAAGACTTT TTTCCAAATC ATTAAACCTG

2961 TTAAATTAAA ATGATTTTGT CAGCCGTATG GCATTATTGT

FIG. 6E.

22025c12, 3336 bases, 672 check
[Strand]

3001 ATACCACTAC TGCCTTTCAT TTGGAATTCA AATGGTTTCC

3041 AATATCCCAA ACTTTGATAC TCTGTTTTCT CAGGAAGTAT

3081 TTGTAGATAA AAATTATTGG TCAGAAAGGT CTGAACTTTT

3121 AAGTTTCTTG TATATTATCC AGTTGTTCTT CTAAAAGGCT

3161 GTATCTACCT GTATTCCAAC TGATGGATTG TAAGAAAATG

3201 TACCAATGTA CCATCACCAA AATTGAGTTT ATTTTTATCT

3241 TTTTAAAATA TTTGCAAATT TGACATATAT GTATGTATAT

3281 ACACAAATAT ATATGTAAAG TGGTTTTCAT TAAATTAGTA

3321 TGCATCCTTT ACTTAC

FIG. 6F.

```
Protein Family / Domain Matches, HMMer version 2
-------------------------------------------------
Query: 22025short
Scores for sequence family classification (score includes all domains):
Model     Description                                    Score     E-value   N
-------   -----------                                    -----     -------   -
PDEase    3'5'-cyclic nucleotide phosphodiesterase       110.8     3.8e-38   1

Parsed for domains:
Model     Domain   seq-f  seq-t    hmm-f  hmm-t       score   E-value
-------   ------   -----  -----    -----  -----       -----   -------
PDEase     1/1      224    308 ..    1     88 [.     110.8   3.8e-38

Alignments of top-scoring domains:
PDEase: domain 1 of 1, from 224 to 308: score 110.8, E = 3.8e-38
                   *->YHNwiHAfdVtQtthILlltalaleryLtdlEvLalvfAAaiHDvDHr
                      YHN  HAA+dVtQ++h+ l+ ++l   Lt+; + + + AAa HDvDH+
    22025short   224  YHNAVHAADVTQAMHCYLKEPKLASFLTPLDIMLGLLAAAAHDVDHP 270

GTnNsFqinsLqkSeLAILYndegSVLEnHHlaqafkLLqd<-*
                      G+n  F+i++  +  LA LY +  SVLEnHH  +++ +L++
    22025short   271  GVNQPFLIKT--NHHLANLYQNM-SVLENHHWRSTIGMLRE    308
```

FIG. 7.

Prosite Pattern Matches for 22025short
Prosite version: Release 12.2 of February 1995

>PS00001/PDOC00001/ASN_GLYCOSYLATION N-glycosylation site.

Query: 107   NSTT   110
Query: 290   NMSV   293

>PS00004/PDOC00004/CAMP_PHOSPHO_SITE cAMP- and cGMP-dependent protein kinase phosphorylation site.

Query: 15   RRWT   18
Query: 94   RRGS   97

>PS00005/PDOC00005/PKC_PHOSPHO_SITE Protein kinase C phosphorylation site.

Query: 117   TKK   119

>PS00006/PDOC00006/CK2_PHOSPHO_SITE Casein kinase II phosphorylation site.

Query: 18    RRGS   21
Query: 56    RRGS   59
Query: 251   TKK    254
Query: 292   TKK    295

>PS00008/PDOC00008/MYRISTYL N-myristoylation site.

Query: 22    GVLPSS   27
Query: 29    GSRPGC   34
Query: 67    GILDNE   72
Query: 258   GLLAAA   263

>PS00009/PDOC00009/AMIDATION Amidation site.

Query: 13   LGRR   16

FIG. 9.

22025, A NOVEL HUMAN CYCLIC NUCLEOTIDE PHOSPHODIESTERASE

CROSS-REFERENCES TO RELATED APPLICATIONS

This application is a continuation-in-part of copending U.S. patent application Ser. No. 09/277,423, filed on Mar. 26, 1999, entitled "Novel Nucleic Acid and Protein Homologs", which is hereby incorporated herein in its entirety by reference.

FIELD OF THE INVENTION

The present invention relates to a newly identified human cyclic nucleotide phosphodiesterase belonging to the superfamily of mammalian phosphodiesterases. The invention also relates to polynucleotides encoding the phosphodiesterase. The invention further relates to methods using the phosphodiesterase polypeptides and polynucleotides as a target for diagnosis and treatment in phosphodiesterase-mediated or -related disorders. The invention further relates to drug-screening methods using the phosphodiesterase polypeptides and polynucleotides to identify agonists and antagonists for diagnosis and treatment. The invention further encompasses agonists and antagonists based on the phosphodiesterase polypeptides and polynucleotides. The invention further relates to procedures for producing the phosphodiesterase polypeptides and polynucleotides.

BACKGROUND OF THE INVENTION

Cyclic nucleotide phosphodiesterases show specificity for purine cyclic nucleotide substrates and catalyze cyclic AMP (cAMP) and cyclic GMP (cGMP) hydrolysis (Thompson W. J. (1991) *Pharma. Ther.* 51:13–33). cyclic nucleotide phosphodiesterases regulate the steady-state levels of cAMP and cGMP and modulate both the amplitude and duration of cyclic nucleotide signal. At least eight different but homologous gene families are currently known to exist in mammalian tissues. Most families contain distinct genes, many of which are expressed in different tissues as functionally unique alternative splice variants. (Beavo (1995) *Physiological Reviews* 75:725–748 and U.S. Pat. No. 5,798,246).

All cyclic nucleotide phosphodiesterases contain a core of about 270 conserved amino acids in the COOH-terminal half of the protein thought to be the catalytic domain of the enzyme. A conserved motif of the sequence HDXXHXX (SEQ ID NO:40) has been identified in the catalytic domain of all cyclic nucleotide phosphodiesterases isolated to date. The cyclic nucleotide phosphodiesterases within each family display about 65% amino acid homology and the similarity drops to less than 40% when compared between different families with most of the similarity occurring in the catalytic domains.

Most cyclic nucleotide phosphodiesterase genes have more than one alternatively spliced mRNA transcribed from them and in many cases the alternative splicing appears to be highly tissue specific, providing a mechanism for selective expression of different cyclic nucleotide phosphodiesterases (Beavo supra). Cell-type-specific expression suggests that the different isozymes are likely to have different cell-type-specific properties.

Type 1 cyclic nucleotide phosphodiesterases are $Ca^{2+}$/calmodulin dependent, are reported to contain three different genes, each of which appears to have at least two different splice variants, and have been found in the lung, heart and brain. Some of the calmodulin-dependent phosphodiesterases are regulated in vitro by phosphorylation/dephosphorylation events. The effect of phosphorylation is to decrease the affinity of the enzyme for calmodulin, which decreases phosphodiesterase activity, thereby increasing the steady state level of cAMP. Type 2 cyclic nucleotide phosphodiesterases are cGMP stimulated, are localized in the brain and are thought to mediate the effects of cAMP on catecholamine secretion. Type 3 cyclic nucleotide phosphodiesterases are cGMP-inhibited, have a high specificity for cAMP as a substrate, and are one of the major phosphodiesterase isozymes present in vascular smooth muscle and play a role in cardiac function. One isozyme of type 3 is regulated by one or more insulin-dependent kinases. Type 4 cyclic nucleotide phosphodiesterases are the predominant isoenzyme in most inflammatory cells, with some of the members being activated by cAMP-dependent phosphorylation. Type 5 cyclic nucleotide phosphodiesterases have traditionally been thought of as regulators of cGMP function but may also affect cAMP function. High levels of type 5 cyclic nucleotide phosphodiesterases are found in most smooth muscle preparations, platelets and kidney. Type 6 cyclic nucleotide phosphodiesterase family members play a role in vision and are regulated by light and cGMP. A Type 7 cyclic nucleotide phosphodiesterase family member is found in high concentrations in skeletal muscle. A listing of cyclic nucleotide phosphodiesterase families 1–7, their localization and physiological role is given in Beavo supra. A Type 8 family is reported in U.S. Pat. No. 5,798,246.

Many functions of the immune and inflammatory responses are inhibited by agents that increase intracellular levels of cAMP (Verghese (1995) *Mol. Pharmacol.* 47:1164–1171) while the metabolism of cGMP is involved in smooth muscle, lung and brain cell function (Thompson W. (1991) *Pharma. Ther.* 51:13–33). A variety of diseases have been attributed to increased cyclic nucleotide phosphodiesterase activity which results in decreased levels of cyclic nucleotides. For example, one form of diabetes insipidus in the mouse has been associated with increased phosphodiesterase Family 4 activity and an increase in low-Km cAMP phosphodiesterase activity has been reported in leukocytes of atopic patients. Defects in cyclic nucleotide phosphodiesterases have also been associated with retinal disease. Retinal degeneration in the rd mouse, human autosomal recessive retinitis pigmentosa, and rod/cone dysplasia 1 in Irish setter dogs has been attributed to mutations in the Family 6 phosphodiesterase, gene B. Family 3 phosphodiesterase has been associated with cardiac disease.

Many inhibitors of different cyclic nucleotide phosphodiesterases have been identified and some have undergone clinical evaluation. For example, Family 3 phosphodiesterase inhibitors are being developed as antithrombotic agents, as antihypertensive agents and as cardiotonic agents useful in the treatment of congestive heart failure. Rolipram, a Family 4 phosphodiesterase inhibitor, has been used in the treatment of depression and other inhibitors of Family 4 phosphodiesterase are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al. (1995) *AIDS* 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al. (1995) *Nat. Med.* 1:244–248) and may be effective in the treatment of tardive dyskinesia (Sasaki et al. (1995) *Eur. J. Pharmacol.* 282:72–76).

There are also nonspecific phosphodiesterase inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al. (1995) *Eur. Respir. J* 8:996–1000) where it is thought to act by inhibiting both cyclic nucleotide phosphodiesterase cAMP and cGMP hydrolysis (Banner et al. (1995) *Monaldi Arch. Chest Dis.* 50:286–292). Pentoxifylline, also known to block TNF-alpha production, may inhibit HIV-1 replication (Angel et al. supra). A list of cyclic nucleotide phosphodiesterase inhibitors is given in Beavo supra.

Cyclic nucleotide phosphodiesterases have also been reported to affect cellular proliferation of a variety of cell types and have been implicated in the treatment of various cancers. (Bang et al. (1994) *Proc. Natl. Acad. Sci. USA* 91:5330–5334) reported that the prostate carcinoma cell lines DU 145 and LNCaP were growth-inhibited by delivery of cAMP derivatives and phosphodiesterase inhibitors and observed a permanent conversion in phenotype from epithelial to neuronal morphology; Matousovic et al. ((1995) *J. Clin. Invest.* 96:401–410) suggest that cyclic nucleotide phosphodiesterase isozyme inhibitors have the potential to regulate mesangial cell proliferation; Joulain et al. ((1995) *J. Mediat. Cell Signal* 11:63–79) reports that cyclic nucleotide phosphodiesterase has been shown to be an important target involved in the control of lymphocyte proliferation; and Deonarain et al. ((1994) *Brit. J. Cancer* 70:786–94) suggest a tumor targeting approach to cancer treatment that involves intracellular delivery of phosphodiesterases to particular cellular compartments, resulting in cell death.

Accordingly, cyclic nucleotide phosphodiesterases are a major target for drug action and development. Accordingly, it is valuable to the field of pharmaceutical development to identify and characterize previously unknown phosphodiesterases. The present invention advances the state of the art by providing a previously unidentified human cyclic nucleotide phosphodiesterase.

SUMMARY OF THE INVENTION

It is an object of the invention to identify novel cyclic nucleotide phosphodiesterases.

It is a further object of the invention to provide novel cyclic nucleotide phosphodiesterase polypeptides that are useful as reagents or targets in phosphodiesterase assays applicable to treatment and diagnosis of cyclic nucleotide phosphodiesterase-mediated or -related disorders.

It is a further object of the invention to provide polynucleotides corresponding to the novel phosphodiesterase polypeptides that are useful as targets and reagents in phosphodiesterase assays applicable to treatment and diagnosis of phosphodiesterase-mediated or -related disorders and useful for producing novel phosphodiesterase polypeptides by recombinant methods.

A specific object of the invention is to identify compounds that act as agonists and antagonists and modulate the expression of the novel phosphodiesterase.

A further specific object of the invention is to provide compounds that modulate expression of the phosphodiesterase for treatment and diagnosis of phosphodiesterase-related disorders.

The invention is thus based on the identification of a novel human cyclic nucleotide phosphodiesterase. The invention encompasses a long and short form of the phosphodiesterase. The amino acid sequence of the longer form is shown in SEQ ID NO:1 and the amino acid sequence of the shorter form is shown as SEQ ID NO:3. The nucleotide sequence of the longer form is shown as SEQ ID NO:2 or SEQ ID NO:4 and the nucleotide sequence of the shorter form is shown as SEQ ID NO:4.

The invention provides isolated phosphodiesterase polypeptides, including a polypeptide having the amino acid sequence shown in SEQ ID NO:1 or SEQ ID NO:3 or the amino acid sequence encoded by the cDNA deposited as ATCC No. PTA-1644 deposited on Apr. 5, 2000.

The invention also provides isolated phosphodiesterase nucleic acid molecules having the sequence shown in SEQ ID NO:2 or SEQ ID NO:4 or in the deposited cDNA.

The invention also provides variant polypeptides having an amino acid sequence that is substantially homologous to the amino acid sequence shown in SEQ ID NO:1 or SEQ ID NO:3 or encoded by the deposited cDNA.

The invention also provides variant nucleic acid sequences that are substantially homologous to the nucleotide sequence shown in SEQ ID NO:2 or SEQ ID NO:4 or in the deposited cDNA.

The invention also provides fragments of the polypeptide shown in SEQ ID NO:1 or SEQ ID NO:3 and nucleotide sequence shown in SEQ ID NO:2 or SEQ ID NO:4, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the phosphodiesterase nucleic acid molecules and polypeptides, and particularly recombinant vectors and host cells.

The invention also provides methods of making the vectors and host cells and methods for using them to produce the phosphodiesterase nucleic acid molecules and polypeptides.

The invention also provides antibodies or antigen-binding fragments thereof that selectively bind the phosphodiesterase polypeptides and fragments.

The invention also provides methods of screening for compounds that modulate expression or activity of the phosphodiesterase polypeptides or nucleic acid (RNA or DNA).

The invention also provides a process for modulating phosphodiesterase polypeptide or nucleic acid expression or activity, especially using the screened compounds. Modulation may be used to treat conditions related to aberrant activity or expression of the phosphodiesterase polypeptides or nucleic acids.

The invention also provides assays for determining the activity of or the presence or absence of the phosphodiesterase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DESCRIPTION OF THE DRAWINGS

FIG. 1 shows the long phosphodiesterase nucleotide sequence (SEQ ID NO:2) and the deduced amino acid sequence (SEQ ID NO:1). It is predicted that amino acids 1–223 constitute the aminoterminal regulatory domain, amino acids 224–462 constitute the catalytic domain, and amino acids 463–502 constitute the carboxyterminal domain.

FIG. 2 shows a comparison of the long phosphodiesterase against the Prosite database of protein patterns, specifically showing a high score against the 3' 5' cyclic nucleotide phosphodiesterase Family 7 (SEQ ID NO:5). The underlined area shows a phosphodiesterase signature.

FIG. 4 shows a hydrophobicity plot of the long phosphodiesterase (SEQ ID NO:1).

FIG. 5 shows an analysis of the long phosphodiesterase open reading frame for amino acids corresponding to specific functional sites. Glycosylation sites are found from about amino acid 107 to about amino acid 110 (SEQ ID NO:7), from about amino acid 290 to about amino acid 293 (SEQ ID NO:8), and from about amino acid 447 to about amino acid 450 (SEQ ID NO:9). A glycosaminoglycan attachment site is found from about amino acid 479 to about amino acid 482 (SEQ ID NO:10). Cyclic AMP and cyclic GMP-dependent protein kinase phosphorylation sites are found from about amino acid 15 to about amino acid 18 (SEQ ID NO:11) and from about amino acid 94 to about amino acid 97 (SEQ ID NO:12). Protein kinase C phosphorylation sites are found from about amino acid 117 to about amino acid 119 and from about amino acid 390 to about amino acid 392. Casein kinase II phophorylation sites are found from about amino acid 18 to about amino acid 21 (SEQ ID NO:13), from about amino 56 to about amino acid 59 (SEQ ID NO:14), from about amino acid 251 to about amino acid 254 (SEQ ID NO:15), from about amino acid 292 to about amino acid 295 (SEQ ID NO:16), from about amino acid 449 to about amino acid 452 (SEQ ID NO:17), from about amino acid 481 to about amino acid 484 (SEQ ID NO:18), and from about amino acid 492 to about amino acid 495 (SEQ ID NO:19). A tyrosine kinase phosphorylation site is found from about amino acid 392 to about amino acid 398 (SEQ ID NO:20). N-myristoylation sites are found from about amino acid 22 to about amino acid 27 (SEQ ID NO:21), from about amino acid 29 to about amino acid 34 (SEQ ID NO:22), from about amino acid 67 to about amino acid 72 (SEQ ID NO:23), from about amino acid 258 to about amino acid 263 (SEQ ID NO:24), and from about amino acid 477 to about amino acid 482 (SEQ ID NO:25). An amidation site is found from about amino acid 13 to about amino acid 16 (SEQ ID NO:26). In addition, amino acids corresponding to the phosphodiesterase signature, HDXXHXX (SEQ ID NO:40), are found in the sequence HDVDHPG at amino acids 265–271 of SEQ ID NO:1.

FIG. 6 shows the short phosphodiesterase nucleotide sequence (SEQ ID NO:4) and the deduced amino acid sequence (SEQ ID NO:3). It is predicted that amino acids 1–223 constitute the amino terminal regulatory domain, and amino acids 224–320 constitute the catalytic domain.

FIG. 7 shows a comparison of the short phosphodiesterase against the Prosite database of protein patterns, specifically showing a high score against the 3' 5' cyclic nucleotide phosphodiesterase Family 7 (SEQ ID NO:6). The underlined area shows a phosphodiesterase signature.

FIG. 9 shows an analysis of the short phosphodiesterase open reading frame for amino acids corresponding to specific functional sites. Glycosylation sites are found from about amino acid 107 to about amino acid 110 (SEQ ID NO:27)and from about amino acid 290 to about amino acid 293 (SEQ ID NO:28). Cyclic AMP and cyclic GMP-dependent protein kinase phosphorylation sites are found from about amino acid 15 to about amino acid 18 (SEQ ID NO:29)and from about amino acid 94 to about amino acid 97 (SEQ ID NO:30). Protein kinase C phosphorylation sites are found from about amino acid 117 to about amino acid 119. Casein kinase II phophorylation sites are found from about amino acid 18 to about amino acid 21 (SEQ ID NO:31), from about amino 56 to about amino acid 59 (SEQ ID NO:32), from about amino acid 251 to about amino acid 254 (SEQ ID NO:33), and from about amino acid 292 to about amino acid 295 (SEQ ID NO:34). N-myristoylation sites are found from about amino acid 22 to about amino acid 27 (SEQ ID NO:35), from about amino acid 29 to about amino acid 34 (SEQ ID NO:36), from about amino acid 67 to about amino acid 72 (SEQ ID NO:37), from about amino acid 258 to about amino acid 263 (SEQ ID NO:38), and an amidation site is found from about amino acid 13 to about amino acid 16 (SEQ ID NO:39). In addition, amino acids corresponding to the phosphodiesterase signature, HDXXHXX (SEQ ID NO:40), are found in the sequence HDVDHPG at amino acids 265–271 of SEQ ID NO:3.

DETAILED DESCRIPTION OF THE INVENTION

Figure 3:
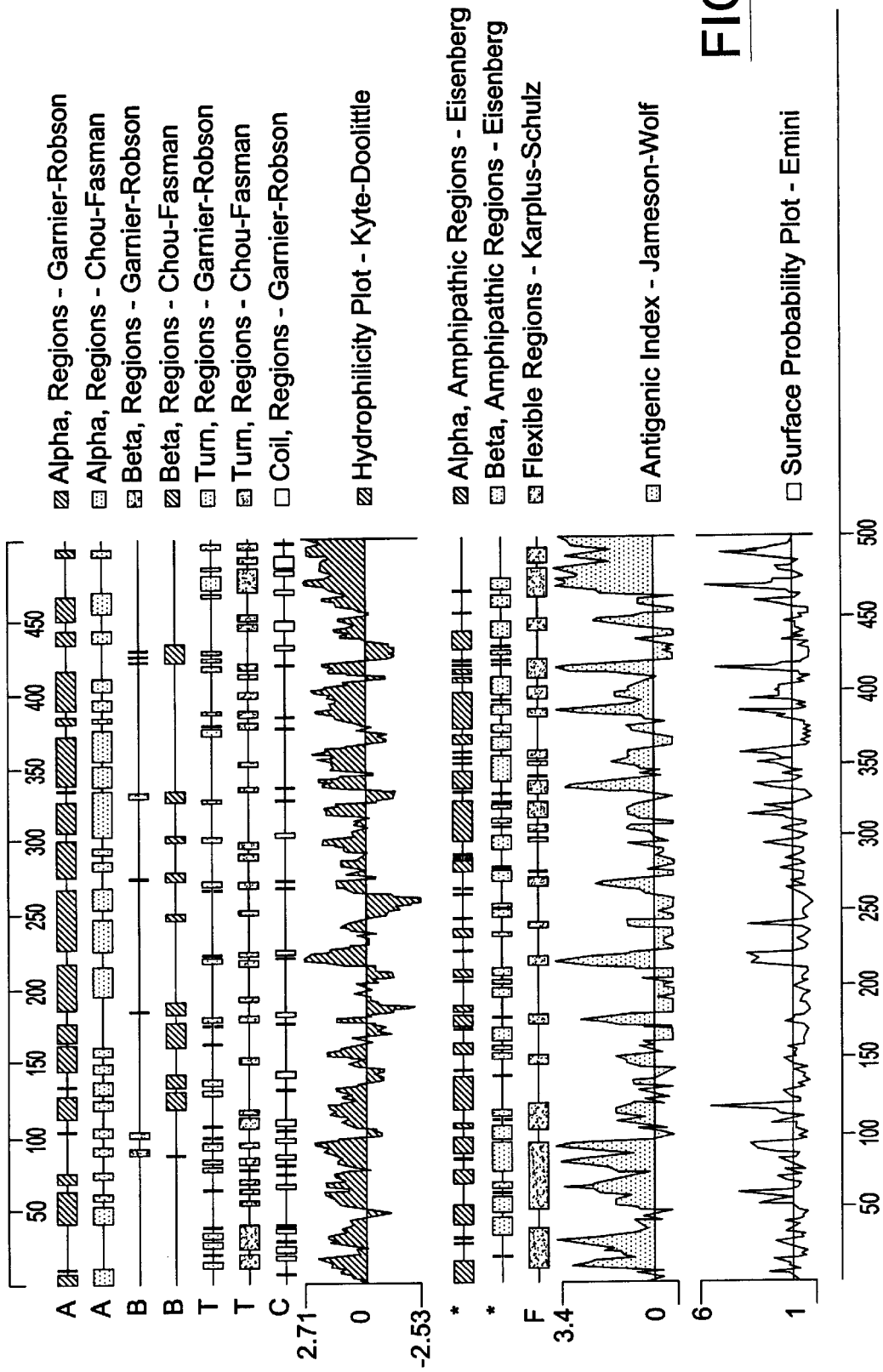
FIG. 3 shows an analysis of the long phosphodiesterase amino acid sequence: αβturn and coil regions; hydrophilicity; amphipathic regions; flexible regions; antigenic index; and surface probability plot.

As used herein, a "signaling pathway" refers to the modulation (e.g., stimulation or inhibition) of a cellular function/activity upon the binding of a ligand to a receptor. Examples of such functions include mobilization of intracellular molecules that participate in a signal transduction pathway, e.g., phosphatidylinositol 4,5-bisphosphate (PIP$_2$), inositol 1,4,5-triphosphate (IP$_3$) and adenylate cyclase; polarization of the plasma membrane; production or secretion of molecules; alteration in the structure of a cellular component; cell proliferation, e.g., synthesis of DNA; cell migration; cell differentiation; and cell survival.

The response depends on the type of cell. In some cells, binding of a ligand to the receptor may stimulate an activity such as release of compounds, gating of a channel, cellular adhesion, migration, differentiation, etc., through phosphatidylinositol or cyclic AMP metabolism and turnover while in other cells, binding will produce a different result.

A signaling pathway is the cAMP turnover pathway. As used herein, "cyclic AMP turnover and metabolism" refers to the molecules involved in the turnover and metabolism of cAMP as well as to the activities of these molecules. Cyclic AMP is a second messenger produced in response to ligand-induced stimulation of certain receptors. In the cAMP signaling pathway, binding of a ligand can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

Polypeptides

The invention is based on the discovery of a novel human cyclic nucleotide phosphodiesterase. Specifically, an expressed sequence tag (EST) was selected based on homology to phosphodiesterase sequences. This EST was used to design primers based on sequences that it contains and used to identify a cDNA from a kidney and adrenal gland cDNA library. Positive clones were sequenced and the overlapping fragments were assembled. Analysis of the assembled sequence revealed that the cloned cDNA molecule encodes a cyclic nucleotide phosphodiesterase. Nucleic acid encoding a truncated form of the enzyme was also isolated from an osteoblast cDNA library.

The invention thus relates to a novel phosphodiesterase having the deduced amino acid sequence shown in FIG. 1 or FIG. 6 (SEQ ID NO:1 or SEQ ID NO:3) or having the amino acid sequence encoded by the deposited cDNA, ATCC No. PTA-1644.

The deposits will be maintained under the terms of the Budapest Treaty on the International Recognition of the Deposit of Microorganisms. The deposits are provided as a convenience to those of skill in the art and is not an admission that a deposit is required under 35 U.S.C. §112. The deposited sequences, as well as the polypeptides encoded by the sequences, are incorporated herein by reference and controls in the event of any conflict, such as a sequencing error, with description in this application.

"Phosphodiesterase polypeptide" or "phosphodiesterase protein" refers to the polypeptides in SEQ ID NO:1 or SEQ ID NO:3 or encoded by the deposited cDNAs. The term "phosphodiesterase protein" or "phosphodiesterase polypeptide", however, further includes the numerous variants described herein, as well as fragments derived from the full-length phosphodiesterases and variants.

Tissues and/or cells in which the phosphodiesterases are found include, but are not limited to heart (including fetal), ovary, brain, pancreas, kidneys, breast, liver, testis, prostate, skeletal muscle, and osteoblasts. In addition, the phosphodiesterases are expressed in diseased tissues, including but limited to, those involved in congestive heart failure and breast cancer. Expression has been confirmed by Northern blot analysis and addition, in osteoblasts, by in situ hybridization.

The present invention thus provides an isolated or purified phosphodiesterase polypeptide and variants and fragments thereof.

The phosphodiesterases include a catalytic signature, HDVDHPG, at residues 265–271. The sequence includes HXXDHXX, a consensus amino acid sequence in cyclic nucleotide phosphodiesterases.

Based on a BLAST search, highest homology was shown to Family 7. The long form is designated B2 and the short form B1.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The phosphodiesterase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the phosphodiesterase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A phosphodiesterase polypeptide is also considered to be isolated when it is part of a membrane preparation or is purified and then reconstituted with membrane vesicles or liposomes.

The language "substantially free of chemical precursors or other chemicals" includes preparations of the phosphodiesterase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the phosphodiesterase polypeptide comprises the amino acid sequence shown in SEQ ID NO:1 or SEQ ID NO:3. However, the invention also encompasses sequence variants. Variants include a substantially homologous protein encoded by the same genetic locus in an organism, i.e., an allelic variant. The phosphodiesterase has been mapped to human chromosome 6 (6q21-q23.2), with flanking markers AFMA074ZG9 (2.6cR) and AFM214ZF6 (7.9cR). Mutations near this locus include, but are not limited to, the following: PPAC, arthropathy, progressive pseudorheumatoid, of childhood; ODDD, oculodentodigital dysplasia; heterocellular hereditary persistence of fetal hemoglobin; DFNA10, deafness, autosomal dominant non-syndromic sensorineural 10; CMD1F, cardiomyopathy, dilated, 1F; and diabetes mellitus, transient neonatal. In the mouse this locus is associated with the following: g1, grey-lethal; d1, downless; Cat5, dominant cataract 5; Lwq3, liver weight QTL 3; mshi, male sterility and histoincompatibility; Mop2, morphine preference 2; H60, histocompatibility 60; Daq4, directional asymmetry QTL 4; Daq5, directional asymmetry QTL, 5; and kd/kidney disease. Genes near this locus include PDNP1 (phosphodiesterase 1/nucleotide pyrophosphatase 1 (homologous to mouseLy-4 1 antigen)), MACS, PTPRK, ARG1, PCMT1, DFNA10, MEKK5, CTGF, SGK, HIVEP2, CMD1F, EPB41L2, HPFH, UTRN, IFNGR1, and ESR1.

Variants also encompass proteins derived from other genetic loci in an organism, but having substantial homology to the phosphodiesterase of SEQ ID NO:1 or SEQ ID NO:3. Variants also include proteins substantially homologous to the phosphodiesterase but derived from another organism, i.e., an ortholog. Variants also include proteins that are substantially homologous to the phosphodiesterase that are produced by chemical synthesis. Variants also include proteins that are substantially homologous to the phosphodiesterase that are produced by recombinant methods. It is understood, however, that variants exclude any amino acid sequences disclosed prior to the invention.

As used herein, two proteins (or a region of the proteins) are substantially homologous when the amino acid sequences are at least about 70–75%, typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NO:2 or SEQ ID NO:4 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 502 amino acid residues, at least 165, preferably at least 200, more preferably at least 250, even more preferably at least 300, and even more preferably at least 350, 400, 450, and 500 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the phosphodiesterase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asni and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |

TABLE 1-continued

Conservative Amino Acid Substitutions.

| Serine |
| Threonine |
| Methionine |
| Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLASST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444–453) algorithm which has been incorporated into the GAP program in the GCG software package using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387) using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to the conserved catalytic region, carboxyterminal regulatory regions, aminoterminal regulatory regions, aminoterminal targeting regions, regions involved in membrane association, regions involved in enzyme activation, for example, by phosphorylation, and regions involved in interaction with components of other cyclic nucleotide (e.g., AMP, GMP)-dependent signal transduction pathways.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the phosphodiesterase polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of cAMP. A further useful variation at the same site can result in altered affinity for cAMP. Useful variations also include changes that provide for affinity for another cyclic nucleotide. Another useful variation includes one that prevents activation by protein kinase A. Another useful variation provides a fusion protein in which one or more domains or subregions are operationally fused to one or more domains or subregions from another phosphodiesterase isoform or family.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as cAMP hydrolysis in vitro or cAMP-dependent in vitro activity, such as proliferative activity. Sites that are critical for cAMP or protein kinase A binding can also be determined by structural analysis such as crystallization, nuclear magnetic resonance or photoaffinity labeling (Smith et al. (1992) *J. Mol. Biol.* 224:899–904; de Vos et al. (1992) *Science* 255:306–312).

Substantial homology can be to the entire nucleic acid or amino acid sequence or to fragments of these sequences.

The invention thus also includes polypeptide fragments of the phosphodiesterase. Fragments can be derived from the amino acid sequence shown in SEQ ID NO:1 or SEQ ID NO:3. However, the invention also encompasses fragments of the variants of the phosphodiesterases as described herein.

The fragments to which the invention pertains, however, are not to be construed as encompassing fragments that may be disclosed prior to the present invention.

Accordingly, a fragment can comprise at least about 10, 15, 20, 25, 30, 35, 40, 45, 50 or more contiguous amino acids. Fragments can retain one or more of the biological activities of the protein, for example the ability to bind to or hydrolyze cAMP, as well as fragments that can be used as an immnunogen to generate phosphodiesterase antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, phosphodiesterase signature, and sites for glycosylation, cAMP and cGMP-dependent protein kinase phosphorylation, protein kinase C phosphorylation, casein kinase II phosphorylation, tyrosine kinase phosphorylation, N-myristoylation, amidation, and glycosaminoglycan attachment. Further possible fragments include the catalytic site or domain including HDXXHXX, an allosteric binding site, sites important for cellular and subcellular targeting, sites functional for interacting with components of other cAMP-dependent signal transduction pathways, and aminoterminal and carboxyterminal regulatory sites.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the phosphodiesterase and variants. These epitope-bearing peptides are useful to raise antibodies that bind specifically to a phosphodiesterase polypeptide or region or fragment. These peptides can contain at least 10, 12, at least 14, or between at least about 15 to about 30 amino acids.

Figure 8:
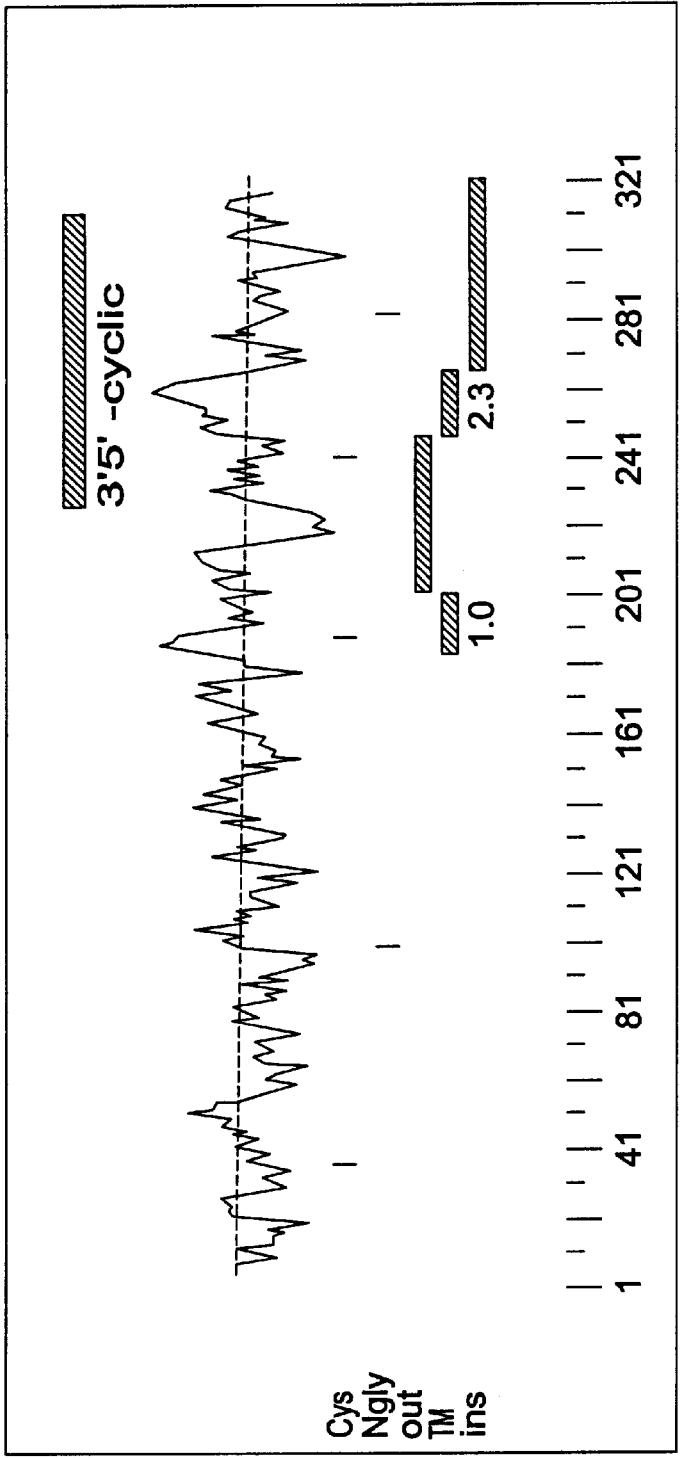
FIG. 8 shows a hydrophobicity plot of the short phosphodiesterase (SEQ ID NO:3).

Non-limiting examples of antigenic polypeptides that can be used to generate antibodies include but are not limited to peptides derived from an extracellular site. Regions having a high antigenicity index are shown in FIGS. 3 and 8. However, intracellularly-made antibodies ("intrabodies") are also encompassed, which would recognize intracellular peptide regions.

The epitope-bearing phosphodiesterase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the phosphodiesterase fragment and an additional region fused to the carboxyl terminus of the fragment.

The invention thus provides chimeric or fusion proteins. These comprise a phosphodiesterase peptide sequence operatively linked to a heterologous peptide having an amino acid sequence not substantially homologous to the phosphodiesterase. "Operatively linked" indicates that the phosphodiesterase peptide and the heterologous peptide are fused in-frame. The heterologous peptide can be fused to the N-terminus or C-terminus of the phosphodiesterase or can be internally located.

In one embodiment the fusion protein does not affect phosphodiesterase function per se. For example, the fusion protein can be a GST-fusion protein in which the phosphodiesterase sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant phosphodiesterase. In certain host cells (e.g., mammalian host cells) expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fe is useful in therapy and diagnosis and thus results, for example, in improved pharmacokinetic properties (EP-A 0232 262). In drug discovery, for example, human proteins have been fused with Fe portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing a phosphodiesterase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A phosphodiesterase-encoding nucleic acid can be cloned into such an expression vector such that the fusion moiety is linked in-frame to the phosphodiesterase.

Another form of fusion protein is one that directly affects phosphodiesterase functions. Accordingly, a phosphodiesterase polypeptide is encompassed by the present invention in which one or more of the phosphodiesterase domains (or parts thereof has been replaced by homologous domains (or parts thereof from another Family 7 phosphodiesterase or other phosphodiesterase family. Accordingly, various permutations are possible. For example, the aminoterminal regulatory domain, or subregion thereof, can be replaced with the domain or subregion from another Family 7 isoform or phosphodiesterase family. As a further example, the catalytic domain or parts thereof, can be replaced; the carboxyterminal domain or subregion can be replaced. Thus, chimeric phosphodiesterases can be formed in which one or more of the native domains or subregions has been replaced by another.

Additionally, chimeric phosphodiesterase proteins can be produced in which one or more functional sites is derived from a different Family 7 isoform, or from another phosphodiesterase family, such as 1–6 and 8. It is understood however that sites could be derived from phosphodiesterase families that occur in the mammalian genome but which have not yet been discovered or characterized. Such sites include but are not limited to the catalytic site, aminoterminal regulatory site, carboxyterminal regulatory site, sites important for targeting to subcellular and cellular locations, sites functional for interaction with components of other cyclic AMP dependent signal transduction pathways, protein kinase A phosphorylation sites, glycosylation sites, and other functional sites disclosed herein.

The isolated phosphodiesterases can be purified from cells that naturally express it, such as from heart (including fetal), ovary, brain, pancreas, kidneys, breast, liver, testis, prostate, skeletal muscle, and osteoblasts, among others, especially purified from cells that have been altered to express it (recombinant), or synthesized using known protein synthesis methods.

In one embodiment, the protein is produced by recombinant DNA techniques. For example, a nucleic acid molecule encoding the phosphodiesterase polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd ed., T. E. Creighton, W. H. Freeman and Company, New York (1993). Many detailed reviews are available on this subject, such as by Wold, F., *Posttransla-* tionail Covalent Modification of Proteins, B. C. Johnson, Ed., Academic Press, New York 1–12 (1983); Seifter et al. (1990) Meth. Enzymol. 182: 626–646) and Rattan et al. (1992) Ann. N.Y. Acad. Sci. 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The phosphodiesterase polypeptides are useful for producing antibodies specific for the phosphodiesterase, regions, or fragments. Regions having a high antigenicity index score are shown in FIGS. 3 and 8.

The phosphodiesterase polypeptides are useful for biological assays related to phosphodiesterases, especially from Family 7. Such assays involve any of the known phosphodiesterase functions or activities or properties useful for diagnosis and treatment of phosphodiesterase-related conditions.

The phosphodiesterase polypeptides are also useful in drug screening assays, in cell-based or cell-free systems.

Cell-based systems can be native, i.e., cells that normally express the phosphodiesterase, as a biopsy or expanded in cell culture. In one embodiment, however, cell-based assays involve recombinant host cells expressing the phosphodiesterase.

Determining the ability of the test compound to interact with the phosphodiesterase can also comprise determining the ability of the test compound to preferentially bind to the polypeptide as compared to the ability of a known binding molecule (e.g. cAMP) to bind to the polypeptide.

The polypeptides can be used to identify compounds that modulate phosphodiesterase activity. Such compounds, for example, can increase or decrease affinity or rate of binding to cAMP, compete with cAMP for binding to the phosphodiesterase, or displace cAMP bound to the phosphodiesterase. Both phosphodiesterase and appropriate variants and fragments can be used in high-throughput screens to assay candidate compounds for the ability to bind to the phosphodiesterase. These compounds can be further screened against a functional phosphodiesterase to determine the effect of the compound on the phosphodiesterase activity. Compounds can be identified that activate (agonist) or inactivate (antagonist) the phosphodiesterase to a desired degree. Modulatory methods can be performed in vitro (e.g., by culturing the cell with the agent) or, alternatively, in vivo (e.g., by administering the agent to a subject.

The phosphodiesterase polypeptides can be used to screen a compound for the ability to stimulate or inhibit interaction between the phosphodiesterase protein and a target molecule that normally interacts with the phosphodiesterase protein. The target can be a cyclic nucleotide or another component of the signal pathway with which the phosphodiesterase protein normally interacts (for example, protein kinase A or other interactor involved in cAMP turnover). The assay includes the steps of combining the phosphodiesterase protein with a candidate compound under conditions that allow the phosphodiesterase protein or fragment to interact with the target molecule, and to detect the formation of a complex between the phosphodiesterase protein and the target or to detect the biochemical consequence of the interaction with the phosphodiesterase and the target, such as any of the associated effects of signal transduction such as protein kinase A phosphorylation, cAMP turnover, and biological endpoints of the pathway.

Determining the ability of the phosphodiesterase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length phosphodiesterase or fragment that competes for cAMP binding. Other candidate compounds include mutant phosphodiesterases or appropriate fragments containing mutations that affect phosphodiesterase function and thus compete for cAMP. Accordingly, a fragment that competes for cAMP, for example with a higher affinity, or a fragment that binds cAMP but does not degrade it, is encompassed by the invention.

The invention provides other end points to identify compounds that modulate (stimulate or inhibit) phosphodiesterase activity. The assays typically involve an assay of events in the signal transduction pathway that indicate phosphodiesterase activity. Thus, the expression of genes that are up- or down-regulated in response to the phosphodiesterase dependent signal cascade can be assayed. In one embodiment, the regulatory region of such genes can be operably linked to a marker that is easily detectable, such as luciferase. Alternatively, phosphorylation of the phosphodiesterase, or a phosphodiesterase target, could also be measured.

Any of the biological or biochemical functions mediated by the phosphodiesterase can be used as an endpoint assay. These include all of the biochemical or biochemical/biological events described herein, in the references cited herein, incorporated by reference for these endpoint assay targets, and other functions known to those of ordinary skill in the art.

In the case of the phosphodiesterase, specific end points can include cAMP hydrolysis and a decrease in protein kinase A activation.

Binding and/or activating compounds can also be screened by using chimeric phosphodiesterase proteins in which one or more domains, sites, and the like, as disclosed herein, or parts thereof, can be replaced by their heterologous counterparts derived from other Family 7 phosphodiesterases or from phosphodiesterase isoforms of any other phosphodiesterase family. For example, a catalytic region can be used that interacts with a different cyclic nucleotide specificity and/or affinity than the native phosphodiesterase. Accordingly, a different set of signal transduction components is available as an end-point assay for activation. Alternatively, a heterologous targeting sequence can replace the native targeting sequence. This will result in different subcellular or cellular localization and accordingly can result in having an effect on a different signal transduction pathway. Accordingly, a different set of signal transduction components is available as an endpoint assay for activation. As a further alternative, the site of modification by an effector protein, for example phosphorylation by protein kinase A, can be replaced with the site from a different effector protein. This could also provide the use of a different signal transduction pathway for endpoint determination. Activation can also be detected by a reporter gene containing an easily detectable coding region operably linked to a transcriptional regulatory sequence that is part of the native signal transduction pathway.

The phosphodiesterase polypeptides are also useful in competition binding assays in methods designed to discover compounds that interact with the phosphodiesterase. Thus, a compound is exposed to a phosphodiesterase polypeptide under conditions that allow the compound to bind or to otherwise interact with the polypeptide. Soluble phosphodiesterase polypeptide is also added to the mixture. If the test compound interacts with the soluble phosphodiesterase polypeptide, it decreases the amount of complex formed or activity from the phosphodiesterase target. This type of assay is particularly useful in cases in which compounds are sought that interact with specific regions of the phosphodiesterase. Thus, the soluble polypeptide that competes with the target phosphodiesterase region is designed to contain peptide sequences corresponding to the region of interest.

Another type of competition-binding assay can be used to discover compounds that interact with specific functional sites. As an example, protein kinase A and a candidate compound can be added to a sample of the phosphodiesterase. Compounds that interact with the phosphodiesterase at the same site as the protein kinase A will reduce the amount of complex formed between the phosphodiesterase and protein kinase A. Accordingly, it is possible to discover a compound that specifically prevents interaction between the phosphodiesterase and protein kinase A. Another example involves adding a candidate compound to a sample of phosphodiesterase and cAMP. A compound that competes with cAMP will reduce the amount of hydrolysis or binding of the cAMP to the phosphodiesterase. Accordingly, compounds can be discovered that directly interact with the phosphodiesterase and compete with cAMP. Such assays can involve any other component that interacts with the phosphodiesterase.

To perform cell free drug screening assays, it is desirable to immobilize either the phosphodiesterase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/phosphodiesterase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of phosphodiesterase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphodiesterase-binding target component, such as cAMP or protein kinase A, and a candidate compound are incubated in the phosphodiesterase-presenting wells and the amount of complex trapped in the well can be quantitated. Methods for detecting such complexes, in addition to those described above for the GST-immobilized complexes, include immunodetection of complexes using antibodies reactive with the phosphodiesterase target molecule, or which are reactive with phosphodiesterase and compete with the target moleculc; as well as enzyme-linked assays which rely on detecting an enzymatic activity associated with the target molecule.

Modulators of phosphodiesterase activity identified according to these drug screening assays can be used to treat a subject with a disorder mediated by the phosphodiesterase pathway, by treating cells that express the phosphodiesterase, such as heart, ovary, brain, pancreas, kidneys, breast, liver, testis, prostate, skeletal muscle, and osteoblast-containing tissue, such as bone. These methods of treatment include the steps of administering the modulators of phosphodiesterase activity in a pharmaceutical composition as described herein, to a subject in need of such treatment.

The phosphodiesterase is expressed in osteoblasts and is involved in osteoblast differentiation. Accordingly, it is involved in bone matrix deposition and thus, bone formation. As such, the gene is particularly relevant for the treatment of disorders involving bone tissue and particularly in osteoporosis.

Disorders in which the phosphodiesterase expression is relevant include, but are not limited to, dementia, memory loss, congestive heart failure, thrombosis, pulmonary hypertension, glomerulonephritis, bipolar depression, bronchial asthma, atopic diseases, autoimmune encephalomyelitis, organ transplantation, salt retention in nephrotic syndrome, and erectile dysfunction.

The phosphodiesterases are also specifically involved in heart disease, such as in congestive heart failure and breast cancer.

The phosphodiesterase polypeptides are thus useful for treating a phosphodiesterase-associated disorder characterized by aberrant expression or activity of a phosphodiesterase. In one embodiment, the method involves administering an agent (e.g., an agent identified by a screening assay described herein), or combination of agents that modulates (e.g., upregulates or downregulates) expression or activity of the protein. In another embodiment, the method involves administering the phosphodiesterase as therapy to compensate for reduced or aberrant expression or activity of the protein.

Methods for treatment include but are not limited to the use of soluble phosphodiesterase or fragments of the phosphodiesterase protein that compete for cAMP or protein kinase A. These phosphodiesterases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoictic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The phosphodiesterase polypeptides also are useful to provide a target for diagnosing a disease or predisposition to disease mediated by the phosphodiesterase, including, but not limited to, diseases involving tissues in which the phosphodiesterases are expressed as disclosed herein, and particularly in osteoporosis, breast cancer, and congestive heart failure. Accordingly, methods are provided for detecting the presence, or levels of, the phosphodiesterase in a cell, tissue, or organism. The method involves contacting a biological sample with a compound capable of interacting with the phosphodiesterase such that the interaction can be detected.

One agent for detecting phosphodiesterase is an antibody capable of selectively binding to phosphodiesterase. A biological sample includes tissues, cells and biological fluids isolated from a subject, as well as tissues, cells and fluids present within a subject.

The phosphodiesterase also provides a target for diagnosing active disease, or predisposition to disease, in a patient having a variant phosphodiesterase. Thus, phosphodiesterase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered phosphodiesterase activity in cell-based or cell-free assay, alteration in cAMP binding or degradation, protein kinase A binding or phosphorylation, or antibody-binding pattern, altered isoelectric point, direct amino acid sequencing, and any other of the known assay techniques useful for detecting mutations in a protein in general or in a phosphodiesterase specifically.

In vitro techniques for detection of phosphodiesterase include enzyme linked immunosorbent assays (ELISAs), Western blots, immunoprecipitations and immunofluorescence. Alternatively, the protein can be detected in vivo in a subject by introducing into the subject a labeled anti-phosphodiesterase antibody. For example, the antibody can be labeled with a radioactive marker whose presence and location in a subject can be detected by standard imaging techniques. Particularly useful are methods, which detect the allelic variant of the phosphodiesterase expressed in a subject, and methods, which detect fragments of the phosphodiesterase in a sample.

The phosphodiesterase polypeptides are also useful in pharmacogenomic analysis. Pharmacogenomics deal with clinically significant hereditary variations in the response to drugs due to altered drug disposition and abnormnal action in affected persons. See, e.g., Eichelbaum, M. (1996) Clin. Exp. Pharmacol. Physiol. 23(10–11):983–985, and Linder, M. W. (1997) Clin. Chem. 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphodiesterase in which one or more of the phosphodiesterase functions in one population is different from those in another population. The polypeptides thus allow a target to ascertain a genetic predisposition that can affect treatment modality. Thus, in a cAMP-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The phosphodiesterase polypeptides are also useful for monitoring therapeutic effects during clinical trials and other treatment. Thus, the therapeutic effectiveness of an agent that is designed to increase or decrease gene expression, protein levels or phosphodiesterase activity can be monitored over the course of treatment using the phosphodiesterase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the phosphodiesterase and its variants and fragments. An antibody is considered to selectively bind, even if it also binds to other proteins that are not substantially homologous with the phosphodiesterase. These other proteins share homology with a fragment or domain of the phosphodiesterase. This conservation in specific regions gives rise to antibodies that bind to both proteins by virtue of the homologous sequence. In this case, it would be understood that antibody binding to the phosphodiesterase is still selective.

To generate antibodies, an isolated phosphodiesterase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 3 or 8.

Antibodies are preferably prepared from these regions or from discrete fragments in these regions. However, antibodies can be prepared from any region of the peptide as described herein. A preferred fragment produces an antibody that diminishes or completely prevents cAMP hydrolysis or binding. Antibodies can be developed against the entire phosphodiesterase or domains of the phosphodiesterase as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, p-galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, or chemically synthesized peptides.

Antibody Uses

The antibodies can be used to isolate a phosphodiesterase by standard techniques, such as affinity chromatography or immunoprecipitation. The antibodies can facilitate the purification of the natural phosphodiesterase from cells and recombinantly produced phosphodiesterase expressed in host cells.

The antibodies are useful to detect the presence of phosphodiesterase in cells or tissues to determine the pattern of expression of the phosphodiesterase among various tissues in an organism and over the course of normal development.

The antibodies can be used to detect phosphodiesterase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length phosphodiesterase can be used to identify phosphodiesterase turnover.

Further, the antibodies can be used to assess phosphodiesterase expression in disease states such as in active stages of the disease or in an individual with a predisposition toward disease related to phosphodiesterase function. When a disorder is caused by an inappropriate tissue distribution, developmental expression, or level of expression of the phosphodiesterase protein, the antibody can be prepared against the normal phosphodiesterase protein. If a disorder is characterized by a specific mutation in the phosphodiesterase, antibodies specific for this mutant protein can be used to assay for the presence of the specific mutant phosphodiesterase. However, intracellularly-made antibodies ("intrabodies") are also encompassed, which would recognize intracellular phosphodiesterase peptide regions.

The antibodies can also be used to assess normal and aberrant subcellular localization of cells in the various tissues in an organism. Antibodies can be developed against the whole phosphodiesterase or portions of the phosphodiesterase.

The diagnostic uses can be applied, not only in genetic testing, but also in monitoring a treatment modality. Accordingly, where treatment is ultimately aimed at correcting phosphodiesterase expression level or the presence of aberrant phosphodiesterases and aberrant tissue distribution or developmental expression, antibodies directed against the phosphodiesterase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic phosphodiesterase can be used to identify individuals that require modified treatment modalities.

The antibodies are also useful as diagnostic tools as an immunological marker for aberrant phosphodiesterase analyzed by electrophoretic mobility, isoelectric point, tryptic peptide digest, and other physical assays known to those in the art.

The antibodies are also useful for tissue typing. Thus, where a specific phosphodiesterase has been correlated with expression in a specific tissue, antibodies that are specific for this phosphodiesterase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting phosphodiesterase function, for example, blocking cAMP, protein kinase A, or the catalytic site.

These uses can also be applied in a therapeutic context in which treatment involves inhibiting phosphodiesterase function. An antibody can be used, for example, to block cAMP binding. Antibodies can be prepared against specific fragments containing sites required for function or against intact phosphodiesterase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a phosphodiesterase protein in a biological sample. The kit can comprise antibodies such as a labeled or labelable antibody and a compound or agent for detecting phosphodicsterase in a biological sample; means for determining the amount of phosphodiesterase in the sample; and means for comparing the amount of phosphodiesterase in the sample with a standard. The compound or agent can be packaged in a suitable container. The kit can further comprise instructions for using the kit to detect phosphodiesterase.

Polynucleotides

The nucleotide sequences in SEQ ID NO:2 or SEQ ID NO:4 were obtained by sequencing the deposited human cDNA. Accordingly, the sequence of the deposited clone is controlling as to any discrepancies between the two and any reference to the sequences of SEQ ID NO:2 or SEQ ID NO:4 includes reference to the sequences of the deposited cDNA.

The specifically disclosed cDNAs comprise the coding region and 5' and 3' untranslated sequences in SEQ ID NO:2 or SEQ ID NO:4.

The invention provides isolated polynucleotides encoding the novel phosphodiesterases. The term "phosphodiesterase polynucleotide" or "phosphodiesterase nucleic acid" refers to the sequences shown in SEQ ID NO:2 or SEQ ID NO:4 or in the deposited cDNAs. The term "phosphodiesterase polynucleotide" or "phosphodiesterase nucleic acid" further includes variants and fragments of the phosphodiesterase polynucleotides.

An "isolated" phosphodiesterase nucleic acid is one that is separated from other nucleic acid present in the natural source of the phosphodiesterase nucleic acid. Preferably, an "isolated" nucleic acid is free of sequences which naturally flank the phosphodiesterase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the phosphodiesterase nucleic acid is isolated from flanking sequences such that it can be subjected to the specific manipulations described herein, such as recombinant expression, preparation of probes and primers, and other uses specific to the phosphodiesterase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The phosphodiesterase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The phosphodiesterase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Phosphodiesterase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

Phosphodiesterase nucleic acid can comprise the nucleotide sequences shown in SEQ ID NO:2 or SEQ ID NO:4, corresponding to human osteoblast (short form) and kidney and adrenal gland (long form) cDNA.

In one embodiment, the phosphodiesterase nucleic acid comprises only the coding region.

The invention further provides variant phosphodiesterase polynucleotides, and fragments thereof, that differ from the nucleotide sequences shown in SEQ ID NO:2 or SEQ ID NO:4 due to degeneracy of the genetic code and thus encode the same protein as that encoded by the nucleotide sequences shown in SEQ ID NO:2 or SEQ ID NO:4.

The invention also provides phosphodiesterase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NO:2 or SEQ ID NO:4 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a phosphodiesterase that is at least about 60–65%, 65–70%, typically at least about 70–75%, more typically at least about 80–85%, and most typically at least about 90–95% or more homologous to the nucleotide sequence shown in SEQ ID NO:2 or SEQ ID NO:4 or a fragment of this sequence. Such nucleic acid molecules can readily be identified as being able to hybridize under stringent conditions, to the nucleotide sequence shown in SEQ ID NO:2 or SEQ ID NO:4 or a fragment of the sequence. It is understood that stringent hybridization does not indicate substantial homology where it is due to general homology, such as poly A sequences or sequences common to all or most proteins, all cyclic nucleotide phosphodiesterases, or all Family 7 phosphodiesterases. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60–65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1–6.3.6, incorporated by reference. One example of stringent hybridization conditions are hybridization in 6× sodium chloride/sodium citrate (SSC) at about 45° C., followed by one or more washes in 0.2× SSC, 0.1% SDS at 50–65° C. In another non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2× SSC/0.1% SDS at 42° C., or washed in 0.2× SSC/0. 1% SDS at 65° C. for high stringency. In one embodiment, an isolated nucleic acid molecule that hybridizes under stringent conditions to the sequence of SEQ ID NO:1 or SEQ ID NO:3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:2 or SEQ ID NO:4 or the complement of SEQ ID NO:2 or SEQ ID NO:4. In one embodiment, the nucleic acid consists of a portion of the nucleotide sequence of SEQ ID NO:2 or SEQ ID NO:4 and the complement of SEQ ID NO:2 or SEQ ID NO:4. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length phosphodiesterase polynucleotides. The fragment can be single or double-stranded and can comprise DNA or RNA. The fragment can be derived from either the coding or the non-coding sequence.

In another embodiment an isolated phosphodiesterase nucleic acid encodes the entire coding region. In another embodiment the isolated phosphodiesterase nucleic acid encodes a sequence corresponding to the mature protein that may be from about amino acid 6 to the last amino acid. Other fragments include nucleotide sequences encoding the amino acid fragments described herein.

Thus, phosphodiesterase nucleic acid fragments further include sequences corresponding to the domains described herein, subregions also described, and specific functional sites. Phosphodiesterase nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that a phosphodiesterase fragment includes any nucleic acid sequence that does not include the entire gene.

The invention also provides phosphodiesterase nucleic acid fragments that encode epitope bearing regions of the phosphodiesterase proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO:2 or SEQ ID NO:4 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The phosphodiesterase polynucleotides are thus useful for probes, primers, and in biological assays.

Where the polynucleotides are used to assess phosphodiesterase properties or functions, such as in the assays described herein, all or less than all of the entire cDNA can be useful. Assays specifically directed to phosphodiesterase functions, such as assessing agonist or antagonist activity, encompass the use of known fragments. Further, diagnostic methods for assessing phosphodiesterase function can also be practiced with any fragment, including those fragments that may have been known prior to the invention. Similarly, in methods involving treatment of phosphodiesterase dysfunction, all fragments are encompassed including those, which may have been known in the art.

The phosphodiesterase polynucleotides are useful as a hybridization probe for cDNA and genomic DNA to isolate a full-length cDNA and genomic clones encoding the polypeptides described in SEQ ID NO:1 or SEQ ID NO:3 and to isolate cDNA and genomic clones that correspond to variants producing the same polypeptides shown in SEQ ID NO:1 or SEQ ID NO:3 or the other variants described herein. Variants can be isolated from the same tissue and organism from which the polypeptides shown in SEQ ID NO:1 or SEQ ID NO:3 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the phosphodiesterase. Accordingly, it could be derived from 5' noncoding regions, the coding region, and 3' noncoding regions. The nucleic acid probe can be, for example, the full-length cDNA of SEQ ID NO:2 or SEQ ID NO:4, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO:2 or SEQ ID NO:4, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med Chem. Lett.* 5:1119.

The nucleic acid molecules and fragments of the invention can also include other appended groups such as peptides (e.g., for targeting host cell phosphodiesterases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The phosphodiesterase polynucleotides are also useful as primers for PCR to amplify any given region of a phosphodiesterase polynucleotide.

The phosphodiesterase polynucleotides are also useful for constructing recombinant vectors. Such vectors include expression vectors that express a portion of, or all of, the phosphodiesterase polypeptides. Vectors also include insertion vectors, used to integrate into another polynucleotide sequence, such as into the cellular genome, to alter in situ expression of phosphodiesterase genes and gene products. For example, an endogenous phosphodiesterase coding sequence can be replaced via homologous recombination with all or part of the coding region containing one or more specifically introduced mutations.

The phosphodiesterase polynucleotides are also useful for expressing antigenic portions of the phosphodiesterase proteins.

The phosphodiesterase polynucleotides are also useful as probes for determining the chromosomal positions of the phosphodiesterase polynucleotides by means of in situ hybridization methods, such as FISH. (For a review of this technique, see Verma et al. (1988) *Human Chromosomes. A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The phosphodiesterase polynucleotide probes are also useful to determine patterns of the presence of the gene encoding the phosphodiesterases and their variants with respect to tissue distribution, for example, whether gene duplication has occurred and whether the duplication occurs in all or only a subset of tissues. The genes can be naturally occurring or can have been introduced into a cell, tissue, or organism exogenously.

The phosphodiesterase polynucleotides are also useful for designing ribozymes corresponding to all, or a part, of the mRNA produced from genes encoding the polynucleotides described herein.

The phosphodiesterase polynucleotides are also useful for constructing host cells expressing a part, or all, of the phosphodiesterase polynucleotides and polypeptides.

The phosphodiesterase polynucleotides are also useful for constructing transgenic animals expressing all, or a part, of the phosphodiesterase polynucleotides and polypeptides.

The phosphodiesterase polynucleotides are also useful for making vectors that express part, or all, of the phosphodiesterase polypeptides.

The phosphodiesterase polynucleotides are also useful as hybridization probes for determining the level of phosphodiesterase nucleic acid expression. Accordingly, the probes can be used to detect the presence of, or to determine levels of, phosphodiesterase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the phosphodiesterase genes.

Alternatively, the probe can be used in an in situ hybridization context to assess the position of extra copies of the phosphodiesterase genes, as on extrachromosomal elements or as integrated into chromosomes in which the phosphodiesterase gene is not normally found, for example as a homogeneously staining region.

These uses are relevant for diagnosis of disorders involving an increase or decrease in phosphodiesterase expression relative to normal, such as a proliferative disorder, a differentiative or developmental disorder, or a hematopoietic disorder.

The phosphodiesterases are expressed in osteoblasts and are involved in osteoblast differentiation. Accordingly, they are involved in bone matrix deposition and thus, bone formation. As such, the gene is particularly relevant for the treatment of disorders involving bone tissue and particularly in osteoporosis.

The phosphodiesterases are also specifically involved in heart disease, such as congestive heart failure, and in breast cancer.

Disorders in which phosphodiesterase expression is relevant also include, but are not limited to, dementia, memory loss, congestive heart failure, thrombosis, pulmonary hypertesion, glomerutonephritis, bipolar depression, bronchial asthma, atopic diseases, autoimmune enceptholomyelitis, organ transplantation, salt retention in nephrotic syndrome, and erectile dysfunction.

Thus, the present invention provides a method for identifying a disease or disorder associated with aberrant expression or activity of phosphodiesterase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the phosphodiesterase, such as by measuring the level of a phosphodiesterase-encoding nucleic acid in a sample of cells from a subject e.g., mRNA or genomic DNA, or determining if the phosphodiesterase gene has been mutated.

Nucleic acid expression assays are useful for drug screening to identify compounds that modulate phosphodiesterase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the phosphodiesterase gene. The method typically includes assaying the ability of the compound to modulate the expression of the phosphodiesterase nucleic acid and thus identifying a compound that can be used to treat a disorder characterized by undesired phosphodiesterase nucleic acid expression.

The assays can be performed in cell-based and cell-free systems. Cell-based assays include cells naturally expressing the phosphodiesterase nucleic acid or recombinant cells genetically engineered to express specific nucleic acid sequences.

Alternatively, candidate compounds can be assayed in vivo in patients or in transgenic animals.

The assay for phosphodiesterase nucleic acid expression can involve direct assay of nucleic acid levels, such as mRNA levels, or on collateral compounds involved in the signal pathway (such as cyclic AMP turnover). Further, the expression of genes that are up- or down-regulated in response to the phosphodiesterase signal pathway can also be assayed. In this embodiment the regulatory regions of these genes can be operably linked to a reporter gene such as luciferase.

Thus, modulators of phosphodiesterase gene expression can be identified in a method wherein a cell is contacted with a candidate compound and the expression of mRNA determined. The level of expression of phosphodiesterase mRNA in the presence of the candidate compound is compared to the level of expression of phosphodiesterase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate phosphodiesterase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

The gene is particularly relevant for the treatment of disorders involving bone tissue and particularly in osteoporosis. The gene is also involved in heart disease, such as congestive heart failure, and in breast cancer. Further disorders in which expression is relevant include, but are not limited to, dementia, memory loss, congestive heart failure, thrombosis, pulmonary hypertesion, glomerulonephritis, bipolar depression, bronchial asthma, atopic diseases, autoimmune encephalomyelitis, organ transplantation, salt retention in nephrotic syndrome, and erectile dysfunction.

Alternatively, a modulator for phosphodiesterase nucleic acid expression can be a small molecule or drug identified using the screening assays described herein as long as the drug or small molecule inhibits the phosphodiesterase nucleic acid expression.

The phosphodiesterase polynucleotides are also useful for monitoring the effectiveness of modulating compounds on the expression or activity of the phosphodiesterase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant.

Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The phosphodiesterase polynucleotides are also useful in diagnostic assays for qualitative changes in phosphodiesterase nucleic acid, and particularly in qualitative changes that lead to pathology. The polynucleotides can be used to detect mutations in phosphodiesterase genes and gene expression products such as mRNA. The polynucleotides can be used as hybridization probes to detect naturally-occurring genetic mutations in the phosphodiesterase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphodiesterase gene associated with a dysfunction provides a diagnostic tool for an active disease or susceptibility to disease when the disease results from overexpression, underexpression, or altered expression of a phosphodiesterase.

Mutations in the phosphodiesterase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. U,SA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a phosphodiesterase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant phosphodiesterase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1 988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mulat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The phosphodiesterase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharnacogenomic relationship). In the present case, for example, a mutation in the phosphodiesterase gene that results in altered affinity for cAMP could result in an excessive or decreased drug effect with standard concentrations of cAMP that activates the phosphodiesterase. Accordingly, the phosphodiesterase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The phosphodiesterase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The phosphodiesterase polynucleotides can also be used to identify individuals from small biological samples. This can be done for example using restriction fragment-length polymorphism (RFLP) to identify an individual. Thus, the polynucleotides described herein are useful as DNA markers for RIJLP (See U.S. Pat. No. 5,272,057).

Furthermore, the phosphodiesterase sequence can be used to provide an alternative technique, which determines the actual DNA sequence of selected fragments in the genome of an individual. Thus, the phosphodiesterase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The phosphodiesterase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The phosphodiesterase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The phosphodiesterase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The phosphodiesterase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of phosphodiesterase probes can be used to identify tissue by species and/or by organ type.

In a similar fashion, these primers and probes can be used to screen tissue culture for contamination (i.e. screen for the presence of a mixture of different types of cells in a culture).

Alternatively, the phosphodiesterase polynucleotides can be used directly to block transcription or translation of phosphodiesterase gene sequences by means of antisense or ribozyme constructs. Thus, in a disorder characterized by abnormally high or undesirable phosphodiesterase gene expression, nucleic acids can be directly used for treatment.

The phosphodiesterase polynucleotides are thus useful as antisense constructs to control phosphodiesterase gene expression in cells, tissues, and organisms. A DNA antisense polynucleotide is designed to be complementary to a region of the gene involved in transcription, preventing transcription and hence production of phosphodiesterase protein. An antisense RNA or DNA polynucleotide would hybridize to the mRNA and thus block translation of mRNA into phosphodiesterase protein.

Examples of antisense molecules useful to inhibit nucleic acid expression include antisense molecules complementary to a fragment of the 5' untranslated region of SEQ ID NO:2 or SEQ ID NO:4 which also includes the start codon and antisense molecules which are complementary to a fragment of the 3' untranslated region of SEQ ID NO:2 or SEQ ID NO:4.

Alternatively, a class of antisense molecules can be used to inactivate mRNA in order to decrease expression of phosphodiesterase nucleic acid. Accordingly, these molecules can treat a disorder characterized by abnormal or undesired phosphodiesterase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphodiesterase protein.

The phosphodiesterase polynucleotides also provide vectors for gene therapy in patients containing cells that are aberrant in phosphodiesterase gene expression. Thus, recombinant cells, which include the patient's cells that have been engineered ex vivo and returned to the patient, are introduced into an individual where the cells produce the desired phosphodiesterase protein to treat the individual.

The invention also encompasses kits for detecting the presence of a phosphodiesterase nucleic acid in a biological sample. For example, the kit can comprise reagents such as a labeled or labelable nucleic acid or agent capable of detecting phosphodiesterase nucleic acid in a biological sample; means for determining the amount of phosphodiesterase nucleic acid in the sample; and means for comparing the amount of phosphodiesterase nucleic acid in the sample with a standard. The compound or agent can be packaged in a suitable container. The kit can further comprise instructions for using the kit to detect phosphodicsterase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the phosphodiesterase polynucleotides. The term "vector" refers to a vehicle, preferably a nucleic acid molecule that can transport the phosphodiesterase polynucleotides. When the vector is a nucleic acid molecule, the phosphodiesterase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC. A vector can be maintained in the host cell as an extrachromosomal element where it replicates and produces additional copies of the phosphodiesterase polynucleotides. Alternatively, the vector may integrate into the host cell genome and produce additional copies of the phosphodiesterase polynucleotides when the host cell replicates.

The invention provides vectors for the maintenance (cloning vectors) or vectors for expression (expression vectors) of the phosphodiesterase polynucleotides. The vectors can function in procaryotic or eukaryotic cells or in both (shuttle vectors).

Expression vectors contain cis-acting regulatory regions that are operably linked in the vector to the phosphodiesterase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the phosphodiesterase polynucleotides from the vector. Alternatively, a trans-acting factor may be supplied by the host cell. Finally, a trans-acting factor can be produced from the vector itself.

It is understood, however, that in some embodiments, transcription and/or translation of the phosphodiesterase polynucleotides can occur in a cell-free system.

The regulatory sequence to which the polynucleotides described herein can be operably linked include promoters for directing mRNA transcription. These include, but are not limited to, the left promoter from bacteriophage X, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals.

The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd ed., Cold Spring Harbor Laboratory Press, Cold Spring Harbor, N.Y.).

A variety of expression vectors can be used to express a phosphodiesterase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning. A Laboratory Manual* 2nd ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The phosphodiesterase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the phosphodiesterase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Phannacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET lid (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1 990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

The phosphodiesterase polynucleotides can also be expressed by expression vectors that are operative in yeast. Examples of vectors for expression in yeast e.g., *S. cerevisiae* include pYepSec1 (Baldari et al. (1987) *EMBO J* 6:229–234 ), pMFa (Kurjan et al. (1982) *Cell* 30:933–943), pJRY88 (Schultz et al. (1987) *Gene* 54:113–123), and pYES2 (Invitrogen Corporation, San Diego, Calif.).

The phosphodiesterase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J*. 6:187–195).

The expression vectors listed herein are provided by way of example only of the well-known vectors available to those of ordinary skill in the art that would be useful to express the phosphodiesterase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual,* 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the phosphodiesterase polynucleotides can be introduced either alone or with other polynucleotides that are not related to the phosphodiesterase polynucleotides such as those providing trans-acting factors for expression vectors. When more than one vector is introduced into a cell, the vectors can be introduced independently, co-introduced or joined to the phosphodiesterase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the phosphodiesterase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing phosphodiesterase proteins or polypeptides that can be further purified to produce desired amounts of phosphodiesterase protein or fragments. Thus, host cells containing expression vectors are useful for polypeptide production.

Host cells are also useful for conducting cell-based assays involving the phosphodiesterase or phosphodiesterase fragments. Thus, a recombinant host cell expressing a native phosphodiesterase is useful to assay for compounds that stimulate or inhibit phosphodiesterase function. This includes cAMP binding, gene expression at the level of transcription or translation, protein kinase A interaction, and components of the signal transduction pathway.

Host cells are also useful for identifying phosphodiesterase mutants in which these functions are affected. If the mutants naturally occur and give rise to a pathology, host cells containing the mutations are useful to assay compounds that have a desired effect on the mutant phosphodiesterase (for example, stimulating or inhibiting function) which may not be indicated by their effect on the native phosphodiesterase.

Recombinant host cells are also useful for expressing the chimeric polypeptides described herein to assess compounds that activate or suppress activation by means of a heterologous domain, segment, site, and the like, as disclosed herein.

Further, mutant phosphodiesterases can be designed in which one or more of the various functions is engineered to be increased or decreased (e.g., cAMP binding or kinase A binding) and used to augment or replace phosphodiesterase proteins in an individual. Thus, host cells can provide a therapeutic benefit by replacing an aberrant phosphodiesterase or providing an aberrant phosphodiesterase that provides a therapeutic result. In one embodiment, the cells provide phosphodiesterases that are abnormally active.

In another embodiment, the cells provide phosphodiesterases that are abnormally inactive. These phosphodiesterases can compete with endogenous phosphodiesterases in the individual.

In another embodiment, cells expressing phosphodiesterases that cannot be activated, are introduced into an individual in order to compete with endogenous phosphodiesterases for cAMP. For example, in the case in which excessive cAMP is part of a treatment modality, it may be necessary to inactivate this molecule at a specific point in treatment. Providing cells that compete for the molecule , but which cannot be affected by phosphodiesterase activation would be beneficial.

Homologously recombinant host cells can also be produced that allow the in situ alteration of endogenous phosphodiesterase polynucleotide sequences in a host cell genome. This technology is more fully described in WO 93/09222, WO 91/12650 and U.S. Pat. No. 5,641,670. Briefly, specific polynucleotide sequences corresponding to the phosphodiesterase polynucleotides or sequences proximal or distal to a phosphodiesterase gene are allowed to integrate into a host cell genome by homologous recombination where expression of the gene can be affected. In one embodiment, regulatory sequences are introduced that either increase or decrease expression of an endogenous sequence. Accordingly, a phosphodiesterase protein can be produced in a cell not normally producing it, or increased expression of phosphodiesterase protein can result in a cell normally producing the protein at a specific level. Alternatively, the entire gene can be deleted. Still further, specific mutations can be introduced into any desired region of the gene to produce mutant phosphodiesterase proteins. Such mutations could be introduced, for example, into the specific regions disclosed herein.

In one embodiment, the host cell can be a fertilized oocyte or embryonic stem cell that can be used to produce a transgenic animal containing the altered phosphodiesterase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous phosphodiesterase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells. A Practical Approach,* E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphodiesterase protein and identifying and evaluating modulators of phosphodiesterase protein activity.

Other examples of transgenic animals include non-human primates, sheep, dogs, cows, goats, chickens, and amphibians.

In one embodiment, a host cell is a fertilized oocyte or an embryonic stem cell into which phosphodiesterase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphodiesterase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phosphodiesterase protein to particular cells.

Methods for generating transgemic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage PI. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxp recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect cAMP binding, phosphodiesterase activation, and signal transduction, may not be evident from in vitro cell-free or cell-based assays. Accordingly, it is useful to provide non-human transgenic animals to assay in vivo phosphodiesterase function, including cAMP interaction, the effect of specific mutant phosphodiesterases on phosphodiesterase function and cAMP interaction, and the effect of chimeric phosphodiesterases. It is also possible to assess the effect of null mutations, that is mutations that substantially or completely eliminate one or more phosphodiesterase functions.

Pharmaceutical Compositions

The phosphodiesterase nucleic acid molecules, protein (such as an extracellular loop), modulators of the protein, and antibodies (also referred to herein as "[]active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer." As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic. Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a phosphodiesterase protein or anti-phosphodiesterase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid. Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) PNAS 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. An isolated nucleic acid molecule having a nucleotide sequence selected from the group consisting of:
   (a) the nucleotide sequence shown in SEQ IN NO:2 or SEQ ID NO:4 and degenerate variants thereof wherein said nucleotide sequence encodes a cyclic nucleotide phosphodiesterase;
   (b) the nucleotide sequence in the cDNA contained in ATCC Deposit No. PTA-1644; and
   (c) a nucleotide sequence complementary to and hybridizing to a unique sequence for any of the nucleotide sequences in (a) or (b) under highly stringent conditions.

2. An isolated nucleic acid molecule having a nucleotide sequence selected from the group consisting of:
   (a) a nucleotide sequence that hybridizes to the entire nucleotide sequence shown in SEQ ID NO:2 or SEQ ID NO:4 under stringent conditions;
   (b) a nucleotide sequence that hybridizes to the cDNA contained in ATCC Deposit PTA-1644 under stringent conditions; and
   (c) a nucleotide sequence complementary to and hybridizing to a unique sequence for ally of the nucleotide sequences in (a) or (b) under highly stringent conditions.

3. An isolated nucleic acid molecule a polynucleotide having a nucleotide sequence selected from the group consisting of:
   (a) a nucleotide sequence encoding a fragment of the amino acid sequence shown in SEQ ID NO:1 or SEQ ID NO:3, wherein the fragment comprises at least 50 contiguous amino acids and retains cyclic nucleotide phosphodiesterase activity;
   (b) a nucleotide sequence encoding a fragment of the amino acid sequence encoded by the cDNA contained in ATCC Deposit No. PTA-1644, wherein the fragment comprises at least 50 contiguous amino acids and retains cyclic phosphodiesterase activity; and
   (c) a nucleotide sequence complementary to and hybridizing to a unique sequence for any of the nucleotide sequences in (a) or (b) under highly stringent conditions.

4. A nucleic acid vector comprising the nucleic acid sequences in any of claims 1–3.

5. A host cell containing the vector of claim 4.

6. An isolated nucleic acid molecule having a nucleotide sequence having at least 70% sequence identity to the nucleotide sequence shown in SEQ ID NO:2 or SEQ ID NO:4 and retains cyclic nucleotide phosphodiesterase activity.

7. An isolated nucleic acid molecule having a nucleotide sequence having at least 80% sequence identity to the nucleotide sequence shown in SEQ TD NO:2 or SEQ ID NO:4 and retains cyclic nucleotide phosphodiesterase activity.

8. An isolated nucleic acid molecule having a nucleotide sequence having at least 90% sequence identity to the nucleotide sequence shown in SEQ ID NO:2 or SEQ ID NO:4 and retains cyclic nucleotide phosphodiesterase activity.

* * * * *

UNITED STATES PATENT AND TRADEMARK OFFICE
CERTIFICATE OF CORRECTION

PATENT NO. : 6,146,876

DATED : November 14, 2000

INVENTOR(S) : Robison et al.

It is certified that error appears in the above-identified patent and that said Letters Patent is hereby corrected as shown below:

Column 1, under Related U.S. Application Data, cancel "Continuation-in-part of application No. 09/277,423, March 26, 1999.

In the References Cited, Other Publications, line 4, "cervisiae" should read --cerevisiae--; line 5, "pp. 12" should read --pp. 12925-12932--.

In Claim 2, column 50, line 11, "ally" should read --any--; line 43, "TD" should read --ID--.

Signed and Sealed this

First Day of May, 2001

Attest:

NICHOLAS P. GODICI

Attesting Officer

Acting Director of the United States Patent and Trademark Office